(12) United States Patent
Wen et al.

(10) Patent No.: US 9,540,418 B2
(45) Date of Patent: Jan. 10, 2017

(54) POLYPEPTIDE SPECIFICALLY BINDING TO RARE EARTH NANOPARTICLES AND USE THEREOF

(71) Applicant: University of Science and Technology of China, Hefei, Anhui (CN)

(72) Inventors: Longping Wen, Anhui (CN); Yunjiao Zhang, Anhui (CN)

(73) Assignee: University of Science and Technology of China, Hefei, Anhui (CN)

( * ) Notice: Subject to any disclaimer, the term of this patent is extended or adjusted under 35 U.S.C. 154(b) by 0 days.

(21) Appl. No.: 14/405,762

(22) PCT Filed: Feb. 6, 2013

(86) PCT No.: PCT/CN2013/071461
§ 371 (c)(1),
(2) Date: Mar. 22, 2015

(87) PCT Pub. No.: WO2013/181947
PCT Pub. Date: Dec. 12, 2013

(65) Prior Publication Data
US 2015/0361135 A1  Dec. 17, 2015

(30) Foreign Application Priority Data

Jun. 7, 2012 (CN) .......................... 2012 1 0185632
Jun. 7, 2012 (CN) .......................... 2012 1 0185635

(51) Int. Cl.
  *C07K 7/06* (2006.01)
  *C07K 7/08* (2006.01)
  *C07K 14/00* (2006.01)
(52) U.S. Cl.
  CPC . *C07K 7/06* (2013.01); *C07K 7/08* (2013.01); *C07K 14/00* (2013.01)
(58) Field of Classification Search
  CPC .............. C07K 7/06; C07K 7/08; C07K 14/00
  See application file for complete search history.

(56) References Cited

U.S. PATENT DOCUMENTS

2006/0172282 A1   8/2006 Naik et al.

FOREIGN PATENT DOCUMENTS

CN        1451958        10/2003

OTHER PUBLICATIONS

Zhang et al, Tuning the autophagy-inducing activity of lanthanide-based nanocrystals through specific surface-coating peptides, Nature Materials, 2012, 11, pp. 817-826.*
Wang et al, Preliminary characterization of a light-rare-earth-element-binding peptide of a natural perennial fern *Dicranopteris dichotoma*, Anal Bioanal Chem, 2003, 376, pp. 49-52.*
Lai et al, Preliminary study of the enrichment and fractionation of REEs in a newly discovered REE hyperaccumulator Pronephrium simplex by SEC-ICP-MS and MALDI-TOF/ESI-MS, J. Anal. At. Spectrom., 2005, 20, pp. 751-753.*
Rudinger, Peptide Hormones, JA Parsons, Ed., 1976, pp. 1-7.*
SIGMA, 2004, pp. 1-2.*
Berendsen, A Glimpse of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
WIPO, "International Search Report of PCT/CN2013/071461," May 16, 2013, (Chinese and English translation) 11 pages.
Cho et al., "The effect of sedimentation and diffusion on cellular uptake of gold nanoparticles," *Nature Nanotechnology*, vol. 6, pp. 385-391, Published online Apr. 24, 2011.

* cited by examiner

*Primary Examiner* — Julie Ha
*Assistant Examiner* — Li Ni Komatsu
(74) *Attorney, Agent, or Firm* — Haynes and Boone, LLP

(57) ABSTRACT

The present invention provides a polypeptide able to specifically bind to rare-earth nanoparticles and the use thereof. The polypeptide comprises an amino acid sequence shown by SEQ ID NO: 1 or analogs thereof. The present invention further provides a method for screening a polypeptide having the capacity of specifically binding to rare-earth nanoparticles. The present invention further provides a method for regulating and controlling the in vivo and in vitro autophagy and toxicity of the rare-earth upconversionnanophosphor material, comprising mixing and incubating the polypeptide specifically binding to rare-earth nanoparticles with rare-earth upconversion nanophosphor material, such that the polypeptide specifically binds to the nanophosphor material, wherein the rare-earth upconversion nanophosphor material comprises the rare earth, and the polypeptide specifically binding to rare-earth nanoparticles comprises the amino acid sequence shown by CTARSPWIC (RE-0, SEQ ID NO: 1) or analogs thereof.

23 Claims, 38 Drawing Sheets

Intensity Distribution

SEQUENCE LISTING

```
<160> NUMBER OF SEQ ID NOS: 35

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Gly Gly Gly Ser
1
```

```
<210> SEQ ID NO 2
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 2

Cys Thr Ala Arg Ser Pro Trp Ile Cys
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 3

Ala Cys Thr Ala Arg Ser Pro Trp Ile Cys Gly
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 4

Ala Cys Trp Pro Ala Thr Arg Ile Ser Cys Gly
1               5                   10

<210> SEQ ID NO 5
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 5

Ala Cys Thr Ala Arg Ser Pro Trp Ile Cys Gly Gly Gly Ala Cys Thr
1               5                   10                  15

Ala Arg Ser Pro Trp Ile Cys Gly
            20

<210> SEQ ID NO 6
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 6

Thr Ala Arg Ser Pro Trp Ile
1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 7

Ala Ala Thr Ala Arg Ser Pro Trp Ile Cys Gly
1               5                   10
```

```
<210> SEQ ID NO 8
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 8

Ala Cys Ala Ala Arg Ser Pro Trp Ile Cys Gly
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 9

Ala Cys Thr Ala Ala Ser Pro Trp Ile Cys Gly
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 10

Ala Cys Thr Ala Arg Ala Pro Trp Ile Cys Gly
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 11

Ala Cys Thr Ala Arg Ser Ala Trp Ile Cys Gly
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 12

Ala Cys Thr Ala Arg Ser Pro Ala Ile Cys Gly
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 13

Ala Cys Thr Ala Arg Ser Pro Trp Ala Cys Gly
1               5                   10
```

```
<210> SEQ ID NO 14
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 14

Ala Cys Thr Ala Arg Ser Pro Trp Ile Ala Gly
1               5                   10

<210> SEQ ID NO 15
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 15

Ala Cys Thr Ala Arg Ser Pro Trp Ile Cys Gly Gly Gly Asn Pro Ser
1               5                   10                  15

Ser Leu Phe Arg Tyr Leu Pro Ser Asp
            20                  25

<210> SEQ ID NO 16
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 16

Asn Pro Ser Ser Leu Phe Arg Tyr Leu Pro Ser Asp
1               5                   10

<210> SEQ ID NO 17
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 17

Arg Lys Leu Pro Asp Ala Gly Gly Gly Ala Cys Thr Ala Arg Ser Pro
1               5                   10                  15

Trp Ile Cys Gly
            20

<210> SEQ ID NO 18
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 18

Arg Lys Leu Pro Asp Ala
1               5

<210> SEQ ID NO 19
<211> LENGTH: 22
<212> TYPE: PRT
<213> ORGANISM: Artificial Sequence
<220> FEATURE:
<223> OTHER INFORMATION: Synthetic Peptide
```

```
<400> SEQUENCE: 19

Cys Leu Ser Tyr Tyr Pro Ser Tyr Gly Gly Ala Cys Thr Ala Arg
1               5                   10                  15

Ser Pro Trp Ile Cys Gly
            20

<210> SEQ ID NO 20
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 20

Cys Leu Ser Tyr Tyr Pro Ser Tyr Cys
1               5

<210> SEQ ID NO 21
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 21

Ser Met Ser Ile Ala Arg Leu Gly Gly Ala Cys Thr Ala Arg Ser Pro
1               5                   10                  15

Trp Ile Cys Gly
            20

<210> SEQ ID NO 22
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 22

Ser Met Ser Ile Ala Arg Leu
1               5

<210> SEQ ID NO 23
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 23

Cys Leu Glu Val Ser Arg Lys Asn Cys Gly Gly Ala Cys Thr Ala Arg
1               5                   10                  15

Ser Pro Trp Ile Cys Gly
            20

<210> SEQ ID NO 24
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 24

Cys Leu Glu Val Ser Arg Lys Asn Cys
1               5
```

<210> SEQ ID NO 25
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 25

Cys Gly Phe Glu Cys Val Arg Gln Cys Pro Glu Arg Cys Gly Gly Ala
1               5                   10                  15

Cys Thr Ala Arg Ser Pro Trp Ile Cys Gly
            20                  25

<210> SEQ ID NO 26
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 26

Cys Gly Phe Glu Cys Val Arg Gln Cys Pro Glu Arg Cys
1               5                   10

<210> SEQ ID NO 27
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 27

Ala Cys Thr Ala Arg Ser Pro Trp Ile Cys Gly Gly Pro Lys Lys Lys
1               5                   10                  15

Arg Lys Val Cys
            20

<210> SEQ ID NO 28
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 28

Pro Lys Lys Lys Arg Lys Val
1               5

<210> SEQ ID NO 29
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 29

Ala Cys Thr Ala Arg Ser Pro Trp Ile Cys Gly Gly Gly Ala Val Pro
1               5                   10                  15

Ile Ala Gln Lys
            20

<210> SEQ ID NO 30
<211> LENGTH: 7
<212> TYPE: PRT
<213> ORGANISM: Artificial Sequence

```
<220> FEATURE:
<223> OTHER INFORMATION: Synthetic Peptide

<400> SEQUENCE: 30

Ala Val Pro Ile Ala Gln Lys
1               5

<210> SEQ ID NO 31
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 31

Cys Arg Gly Asp Cys Gly Gly Ala Cys Thr Ala Arg Ser Pro Trp Ile
1               5                   10                  15

Cys Gly

<210> SEQ ID NO 32
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 32

Cys Asn Ala Thr Leu Pro His Gln Cys
1               5

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 33
cgaggtcgcc ttggatttgc                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 34
gaccagtcgc atccgcagca                                               20

<210> SEQ ID NO 35
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 35

Ala Cys Asn Ala Thr Leu Pro His Gln Cys Gly
1               5                   10
```

POLYPEPTIDE SPECIFICALLY BINDING TO RARE EARTH NANOPARTICLES AND USE THEREOF

CROSS-REFERENCE TO RELATED APPLICATIONS

This is the national stage of PCT/CN2013/071461, filed Feb. 6, 2013, which claims the benefit of CN201210185635.4, filed Jun. 7, 2012; and CN201210185632.0, filed Jun. 7, 2012; the contents of each of which is hereby incorporated herein in its entirety by express reference thereto.

TECHNICAL FIELD

The present invention relates to nanobiology, and more specifically, to a polypeptide specifically binding to rare-earth nanoparticles and the use thereof.

BACKGROUND

Rare earth-based upconversion nanophosphors (UCN), as one of the new generation of bioluminescence labels, have advantages of good light and chemical stability, narrow absorption and emission bands, long luminescence life, and reduced risk of potential bio-toxicity and the like, compared to downconversion luminescence labels such as organic fluorescent dyes, quantum dots, and the like. Upconversion luminescence labels have great advantages such as deeper optical penetration depth, no fluorescence interference caused by biological background, and almost no harm to tissues due to the use of near infrared continuous laser as excitation source, which make it an ideal label for biological imaging. Further, since rare-earth upconversion nanomaterials are rare earth nanoparticles doped with fluorides, they have lower phonon energy, and may reduce non-radiative transition and increase luminescence intensity. Accordingly, among various substances such as oxides, sulfides, phosphides and the like, UCN has recently been widely used for analytic detection and the treatment of diseases and the like.

However, the use of rare-earth upconversion nanoparticles, as inorganic nanoparticles, for in vivo application and clinical test, may lead to many problems. For example, the nanoparticles are prone to agglomeration and not soluble in water, and thus can not be used in in vivo environment; when used for in vivo biological imaging and photodynamic therapy, the nanoparticles may non-specifically attach to a number of tissues, cells, and biomolecules, which may affect the effects to be obtained; when they are introduced into cells or animal bodies, the nanoparticles may result in serious autophagy of cells, or even death of cells and the like.

Recently, the surface modification of inorganic nanoparticles is mainly achieved in a covalent and non-covalent way, by using silica gel (CN101434748), fatty acids (CN1400167), PEG (CN101038290), chitosan (CN101411893), proteins, polypeptides, and the like to modify the surface characteristics of nanoparticles. Among others, the method of coating with a specific binding peptide is a preferred method for surface modification. The method results in significant multifunctionality, biocompatibility, simplicity, and expansibility. Recently, the specific-binding polypeptides, which are mainly reported nationally and internationally, are mainly binding to tissues, organs, cells, and proteins in vitro or in vivo. Examples of such polypeptides are polypeptides specifically binding to normal or cancerous tissues and organs (CN101531706, CN101827583A, CN1563078, CN102060909A, CN101891803A); polypeptides specifically binding to normal or cancerous cells (CN101918433A, CN1709905, CN1763082, CN101033251, CN1900108); and polypeptides specifically binding to proteins in vivo (CN102060913A, CN1823087, CN1262688, CN102105487A, CN101146822, CN1721432, CN1687128, CN101225108, CN101113164, CN101481418). However, polypeptides specifically binding to inorganic nanoparticles have been rarely reported. Only reported are polypeptides specifically binding to titanium, silver, and silicon (CN1829734) and polypeptides binding to nickel with high affinity (CN1911956).

Further, a common biological effect in nanomaterials has been discovered in recent studies, i.e., when they are introduced into cells, nanomaterials result in an abnormally increased level of autophagy of the cells. Cell autophagy is a stress response of cells to outside stimulation such as deficiency of nutrients and the like, in which a double-layer membrane structure is formed to encapsulate part of cytoplasm and organelles into autophagosomes which then fuse with lysosomes to form autophagy lysosomes, in which the contents are digested and reused. Therefore, the cell autophagy caused by nanomaterials is a double-edged sword. With the quick development of nano-technology, an increasing number of nanomaterials are introduced into human body with or without intention. Potential autophagy probably caused by these nanomaterials may have safety risks on human health. In addition, autophagy is closely associated with the occurrence and development of severe diseases. Regulation of autophagy caused by nanomaterials widely used for biomedical diagnosis and treatment may facilitate the use of nanomaterials for the diagnosis and treatment of diseases such as cancer.

Recently, the studies on the regulation of autophagy are mainly focused on the regulation of the level of autophagy per se. For example, autophagy revulsants, Dihydroartemisinin (CN102038678A), the complexes of manganese with dipicolylamine ligands targeting mitochondrion (CN101392007), 4-benzothiopheneaminoquinazoline derivatives (CN101836992A), β-carboline ruthenium complex (CN101845060A), plant viruses (tobacco mosaic virus) (CN101653462), rapamycin (CN102274219A), nonreceptor tyrosine kinase c-Abl specific inhibitor (CN1899616), hydroxytyrosol (CN102397268A); and some autophagy inhibitors, Bafilomysin A1 (CN101953845A), 3-methyladenine, SB203580, LY294002, or wortmannin (CN101869568A), chloroquine (CN101920015A), hydroxychlorquine (CN101428025) are used. However, no study on the regulation of autophagy caused by inorganic nanomaterials has been reported.

Therefore, there is an urgent need for the development of polypeptides able to specifically bind to rare-earth nanoparticles, and for the development of a method of regulating (including increasing and reducing) autophagy and toxicity caused by the use of rare-earth nanomaterials (especially, upconversion nanomaterials) in vitro and in vivo.

DESCRIPTION

To solve the above-mentioned technical problem, the present invention provides a method for screening polypeptides able to specifically bind to rare-earth nanoparticles by using phage display technique and phage display library, the method comprising the steps of: (a) mixing and incubating phage display polypeptide library with rare-earth nanoparticles; (b) recovering phages binding to the rare-earth nanoparticles; (c) amplifying the recovered phages for the next round of rare-earth nanoparticles binding screening; (d) repeating the steps (a) to (c) at least twice; and (e) picking out the monoclones of the recovered phages and sequencing to obtain the encoded displayed polypeptides.

The phage display polypeptide library, which is purchased from New England Biolabs (Ipswich, Mass., USA, Cat. No.: E8120S), is a disulfide-containing heptapeptide library (Ph.D.-C7C). In this library, the randomized fragment is flanked by a pair of cysteine residues at both ends. They can be oxidized to form a disulfide bridge during phage assembly, resulting in a cyclized peptide, which may interact with the target. This library comprises more than 2,000,000,000 clones. Randomized peptides in the library are at the N-terminus of the small envelop protein pIII, and thus each phage particle expresses five copies. The position where the randomized sequence is expressed by phage in Ph.D.-C7C library is preceded by Ala-Cys. A short spacer (Gly-Gly-Gly-Ser) (SEQ ID NO:1) is between the randomized peptide and pIII protein. For more details of Ph.D.™-C7C phage-display polypeptide kit, see the manufacturer's website.

The rare-earth nanoparticles are not particularly limited. The rare-earth nanoparticles include, but not limited to, rare-earth metal oxide, rare-earth metal sulfide, rare-earth metal sulfoxide, rare-earth element-based rare-earth upconversion nanophosphors and any compound comprising rare earth elements. The rare-earth upconversion nanophosphors, for example, UCN (upconvertion nanocrystals) having a particle size of 100 nm, UCP (upconvertion particles) having a particle size of 500 nm, and UCN-S (upconvertion nanocrystals-small) having a particle size of 20 nm, can be used. In a preferred embodiment, the rare-earth nanoparticles used in the present invention are $Nd_2O_3$ nanoparticles.

In one aspect, the polypeptide-displaying phages identified by the method of the present invention have a nucleotide sequence encoding displayed polypeptide CTARSPWIC (RE-0, SEQ ID NO:2). The phages carrying this displayed polypeptide exhibit the ability of specifically binding to rare-earth nanoparticles with high affinity. Thus, the present invention provides a polypeptide specifically binding to rare-earth nanoparticles, wherein the polypeptide comprises an amino acid sequence as shown by SEQ ID NO:2 or its analogues.

In another aspect, the present invention further provides a method for chemically synthesizing a polypeptide specifically binding to rare-earth nanoparticles with high affinity or its analogues. The analogues comprise amino acid sequences screened and identified by phage display technique. The polypeptide of the present invention and its analogues comprising the amino acid sequence of peptide displayed by phages exhibit the ability of binding to rare-earth nanomaterials with high specificity. The rare-earth nanomaterials include rare-earth metal oxides, rare-earth metal sulfides, rare-earth metal sulfoxides, rare-earth element-based rare-earth upconversion nanophosphors and any compound comprising rare earth elements. Methods for producing polypeptides or proteins well-known to those skilled in the art include, but not limited to, expressing peptides or proteins by using standard molecular biology techniques such as recombination expression and the like, extracting peptides or proteins from natural sources, or chemically synthesizing peptides or proteins, which are all within the scope of the present invention.

In a preferred example, a polypeptide consisting of a sequence of ACTARSPWICG (RE-1, SEQ ID NO:3) is synthesized. RE-1 comprises the sequence of RE-0 (CTARSPWIC, SEQ ID NO:2), that is, the sequence of RE-0 derived from the envelop proteins of phage M13 is added two terminal amino acids A and G. In other examples, the analogues of the polypeptide RE-1 are also synthesized. These analogues include RE-3 (ACWPATRISCG, SEQ ID NO:4), which has the same two amino acids at either terminus of RE-1 with the order of 7 amino acids therebetween being disrupted; RE-2X (ACTARSPWICGGGACTARSPWICG, SEQ ID NO:5), which consists of two RE-1s. It has been demonstrated that these polypeptides and the analogues thereof are able to specifically bind to rare-earth nanomaterials with high affinity.

In other examples, other analogues of the polypeptide RE-1 are also synthesized. These analogues include RE-2 (TARSPWI, SEQ ID NO:6), which is formed by removing the two amino acids at either terminus of RE-1 and keeping the 7 amino acids therebetween; RE-4 (AATARSPWICG, SEQ ID NO:7), which is formed by substituting one amino acid in RE-1 (2C→A); RE-5 (ACAARSPWICG, SEQ ID NO:8), which is formed by substituting one amino acid in RE-1 (3T→A); RE-6 (ACTAASPWICG, SEQ ID NO:9), which is formed by substituting one amino acid in RE-1 (5R→A); RE-7 (ACTARAPWICG, SEQ ID NO:10), which is formed by substituting one amino acid in RE-1 (6S→A); RE-8 (ACTARSAWICG, SEQ ID NO:11), which is formed by substituting one amino acid in RE-1 (7P→A); RE-9 (ACTARSPAICG, SEQ ID NO:12), which is formed by substituting one amino acid in RE-1 (8W→A); RE-10 (ACTARSPWACG, SEQ ID NO:13), which is formed by substituting one amino acid in RE-1 (9I→A); and RE-11 (ACTARSPWIAG, SEQ ID NO:14), which is formed by substituting one amino acid in RE-1 (10C→A). It has been demonstrated that these polypeptides and the analogues thereof are able to specifically bind to rare-earth nanomaterials with high affinity.

The polypeptide of the present invention may further be connected to sequences such as specific metal-binding peptide, specific cell-targeting peptide, specific tissue-targeting peptide, nucleic acid-localizing peptide, specific tumor cell-targeting sequence, such that the polypeptide of the present invention has multifunction.

In other examples, the analogues of RE-1 are also synthesized. The analogues include RE-Ag (ACTARSPWICGGGNPSSLFRYLPSD, SEQ ID NO:15), which consists of RE-1 and a specific metal silver-binding peptide (NPSSLFRYLPSD) (SEQ ID NO:16), and has been shown to be able to specifically bind to rare-earth nanoparticles and metal silver with high affinity simultaneously; RE-Ti (RKLPDAGGGACTARSPWICG, SEQ ID NO:17), which consists of RE-1 and a specific metal titanium-binding peptide (RKLPDA) (SEQ ID NO:18), and has been shown to be able to specifically bind to rare-earth nanoparticles and metal titanium with high affinity simultaneously; RE-AT (CLSYYPSYCGGACTARSPWICG, SEQ ID NO:19), which consists of RE-1 and apoptotic cell-targeting peptide (CLSYYPSYC) (SEQ ID NO:20), and has been shown to be able to not only specifically bind to rare-earth nanoparticles with high affinity, but also to target the rare-earth nanoparticles to the surface of apoptotic cells; RE-PH (SMSIARLGGACTARSPWICG, SEQ ID NO:21), which consists of RE-1 and prostate-homing peptide (SMSIARL) (SEQ ID NO:22), and has been shown to be able to not only specifically bind to rare-earth nanoparticles with high affinity, but also to target the rare-earth nanoparticles to prostate tissue; RE-BH (CLEVSRKNCGGACTARSPWICG, SEQ ID NO:23), which consists of RE-1 and brain-homing peptide (CLEVSRKNC) (SEQ ID NO:24), and has been shown to be able to not only specifically bind to rare-earth nanoparticles with high affinity, but also to target the rare-earth nanoparticles to brain; RE-LH (CGFECVRQCPERCGGACTARSPWICG, SEQ ID NO:25), which consists of RE-1 and lung-homing peptide (CGFECVRQCPERC) (SEQ ID NO:26), and has been shown to be able to not only specifically bind to rare-earth nanoparticles with high affinity, but also to target the rare-earth nanoparticles to lung; RE-DH (ACTARSPWICGGPKKKRKVC, SEQ ID NO:27), which consists of RE-1 and nucleic acid-localizing peptide (PKKKRKV) (SEQ ID NO:28), and has been shown to be able to not only specifically bind to rare-earth nanoparticles with high affinity, but also to target the rare-earth nanoparticles to nucleus; RE-SMAC (ACTARSPWICGGGAVPIAQK, SEQ ID NO:29), which consists of RE-1 and pro-apoptosis polypeptide SMAC (AVPIAQK) (SEQ ID NO:30), and has been shown to be able to not only specifically bind to rare-earth nanoparticles with high affinity, but also to target the rare-earth nanoparticles to apoptotic cells; RE-1-RGD (CRGDCGGACTARSPWICG, SEQ ID NO:31), which consists of RE-1 and tumor cell-targeting peptide RGD, and has been shown to be able to not only specifically bind to rare-earth nanoparticles with high affinity, but also to target the rare-earth nanoparticles to tumor cells.

The present invention further provides nucleotide sequences encoding the polypeptides of the present invention and the analogues thereof, which are able to specifically bind to rare-earth nanoparticles. The polypeptides of the present invention which are able to specifically bind to rare-earth nanoparticles, such as polypeptides RE-0 (SEQ ID NO:2), RE-1 (SEQ ID NO:3), RE-2X (SEQ ID NO:5), and RE-3 (SEQ ID NO:4), or the fragments, homologs, and analogues thereof, are all able to specifically bind to rare-earth nanoparticles with high affinity. The present invention further provides nucleotide sequences, which may be hybridized with the nucleotide sequences encoding the polypeptides of the present invention and the analogs or fragments thereof, which are able to specifically bind to rare-earth nanoparticles under strict conditions. Further, nucleotide sequences complementary to the nucleotide sequences as described above are also within the scope of the present invention.

In further studies, the present inventor surprisingly found that the polypeptides obtained by screening, which are able to specifically bind to rare-earth nanoparticles, can regulate (including "reduce" and "increase") the autophagy and toxicity caused by rare-earth upconversion nanophosphors. This is a surprising finding.

Thus, the present invention further provides the use of the specific rare-earth nanoparticle-binding polypeptides for regulating autophagy and toxicity caused by rare-earth upconversion nanophosphors in vivo and in vitro, including mixing and incubating the polypeptides with rare-earth upconversion nanophosphors, such that the polypeptides specifically bind to the nanophosphors, wherein, the rare-earth upconversion nanophosphors comprise rare earth, and the polypeptides specifically binding to the rare-earth nanoparticles comprise an amino acid sequence shown by CTARSPWIC (RE-0, SEQ ID NO:2) or its analogues.

In another aspect, the present invention further provides a method for regulating the autophagy and toxicity caused by rare-earth upconversion nanophosphors in vivo and in vitro, the method comprising: mixing and incubating the polypeptides of the invention obtained by screening, which are able to specifically bind to rare-earth nanoparticles, with the rare-earth upconversion nanophosphors, such that the polypeptides specifically bind to the nanophosphors, wherein, the rare-earth upconversion nanophosphors comprise rare-earth, and the polypeptides specifically binding to the rare-earth nanoparticles comprise an amino acid sequence shown by CTARSPWIC (RE-0, SEQ ID NO:2) or its analogues.

The present invention further provides a method for evaluating the suspension ability of a nanomaterial, comprising the steps of: (a) adding the suspension of the nanomaterial into a UV detection cell; (b) detecting and scanning, in real time, the nanomaterial in the detection cell at the characteristic UV absorption wavelength of the nanomaterial to obtain time-dynamics curve; and (c) evaluating the suspension ability of the nanomaterial in accordance with the time-dynamics curve.

The present invention further provides a method for evaluating the sedimentation rate and diffusibility of a nanomaterial and its interaction with cells, comprising the steps of: (a) culturing the cells on a coverslip, and then placing the coverslip into a cell culturing plate with the cells facing upward or downward, wherein the coverslip is supported by a glass cube; (b) pouring culturing medium comprising the nanomaterial into the cell culturing plate, such that the cells are completely immersed into the medium, wherein the coverslip is just located at the middle of the height of the medium; (c) observing the nanomaterial adhered to the cell surface under a fluorescence microscope equipped with an infrared laser; and (d) evaluating the sedimentation rate and diffusibility of the nanomaterial and its interaction with cells in accordance with observation results under the fluorescence microscope.

The present invention further provides a device for evaluating the sedimentation rate and diffusibility of a nanomaterial and its interaction with cells, comprising: a cell culturing plate, a coverslip, and a glass cube, wherein the glass cube is located in the cell culturing plate, and the coverslip is supported by the glass cube.

The present invention further provides other uses of the specific rare-earth nanoparticle-binding polypeptides of the present invention, which are screened for specifically binding to rare-earth nanoparticles with high affinity. The polypeptides can bind to the surface of the nanoparticle to form a coating layer for improving the suspension ability of the rare-earth nanoparticles in water, preventing the agglomeration of the particles, reducing the interaction between the particles, and reducing nonspecific adherence between the rare-earth nanoparticles and the surfaces of cells, the surface of a cell culturing plate, and the surfaces of other media.

In a preferred aspect, the present invention provides a method for improving the suspension ability of rare-earth nanoparticles in water, comprising the step of binding the specific rare-earth nanoparticle-binding polypeptides of the present invention to the surface of the rare-earth nanoparticles to form a coating layer.

In another preferred aspect, the present invention provides a method for reducing nonspecific adherence between the rare-earth nanoparticles and the surfaces of cells, the surface of a cell culture plate, and the surfaces of other media, comprising the step of binding the specific rare-earth nanoparticle-binding polypeptides of the present invention to the surface of the rare-earth nanoparticles to form a coating layer.

By surface-modifying rare-earth upconversion nanophosphors with the polypeptides of the present invention which specifically bind to rare-earth nanoparticles with high affinity, autophagy induced by rare-earth upconversion nanophosphors in cells and organ tissues (for example, HeLa cells and the liver of Balb/c mice) is reduced, toxicity and liver damage caused by rare-earth upconversion nanophosphors is further reduced, and the safety of such nanomaterials is improved.

Further, by connecting the polypeptides of the present invention which specifically bind to rare-earth nanoparticles with high affinity to tumor cell-targeting sequence RGD to form a difunctional polypeptide RE-1-RGD, the ability of rare-earth upconversion nanophosphors in inducing cell autophagy is increased, the toxicity of the nanomaterials in tumor cells is further increased, and the therapeutic effect of the nanomaterials is improved.

BRIEF DESCRIPTION OF THE DRAWINGS

FIG. 5A is a transmission electron microscope photograph showing the binding of UCN to RE-1 peptide. FIG. 5B is a transmission electron microscope photograph showing the binding of UCN to REOB-1 phage. FIG. 5C is a scanning electron microscope photograph showing the binding of UCN to RE-1 peptide.

FIG. 6A is a graph showing the particle size distribution of UCN. FIG. 6B is a graph showing the particle size distribution of UCP. FIG. 6C is a graph showing the particle size distribution of UCN-S.

FIG. 7A (UCN) and FIG. 7B (UCP) are plotted as binding vs. time, and FIG. 7C (UCN), FIG. 7D (UCP) and FIG. 7E (UCN-S) are plotted as binding vs. concentration.

FIG. 8A (UCN) and FIG. 8B (UCP) show the effect of pH. FIG. 8C (UCN) and FIG. 8D (UCP) show the effect of ion concentration. FIG. 8E (UCN) and FIG. 8F (UCP) show the effect of temperature.

FIG. 9A shows the dissociation from UCN. FIG. 9B shows the dissociation from UCP.

FIG. 10A is a time-dynamics curve for UCN. FIG. 10B is a time-dynamics curve for UCP.

FIG. 11A and FIG. 11B show the results for UCN. FIG. 11C and FIG. 11D show the results for UCN-S.

FIG. 12A and FIG. 12B are schematic views of experimental device. FIG. 12C, FIG. 12D, and FIG. 12E show the results for UCN. FIG. 12F, FIG. 12G, and FIG. 12H show the results for UCP.

FIG. 14A, FIG. 14B, and FIG. 14C show the results for UCN. FIG. 14D, FIG. 14E, and FIG. 14F show the results for UCP. FIG. 14G and FIG. 14H show the results for UCN-S.

FIG. 15A, FIG. 15B, and FIG. 15C show the results for UCN. FIG. 15D, FIG. 15E, and FIG. 15F show the results for UCP.

FIG. 16A shows the results for UCN. FIG. 16B shows the results for UCP.

FIG. 17A shows the results for UCN. FIG. 17B shows the results for UCP.

FIG. 18A shows the results for UCN. FIG. 18B shows the results for UCP.

FIG. 19A shows the results for UCN. FIG. 19B shows the results for UCP.

FIG. 20A shows the MTT results for UCN. FIG. 20B shows the PI staining results for UCN. FIG. 20C shows the MTT results for UCP. FIG. 20D shows the PI staining results for UCP.

FIG. 21A shows the results for UCN. FIG. 21B shows the results for UCP.

FIG. 24A, LC3 dot-like aggregates and vacuoles in cells in RE-1-RGD-coated UCN group are significantly increased compared to UCN group, indicating that RE-1-RGD may specifically target the cells, increase autophagy, and thus increase the therapeutic effect of UCN. FIG. 24B, LC3II in the cells is significantly increased in RE-1-RGD-coated UCN group, indicating that RE-1-RGD may increase the level of autophagy induced by UCN.

FIG. 25A shows the MTT results. FIG. 25B shows the PI staining results.

SPECIFIC EMBODIMENTS

Figure 1:
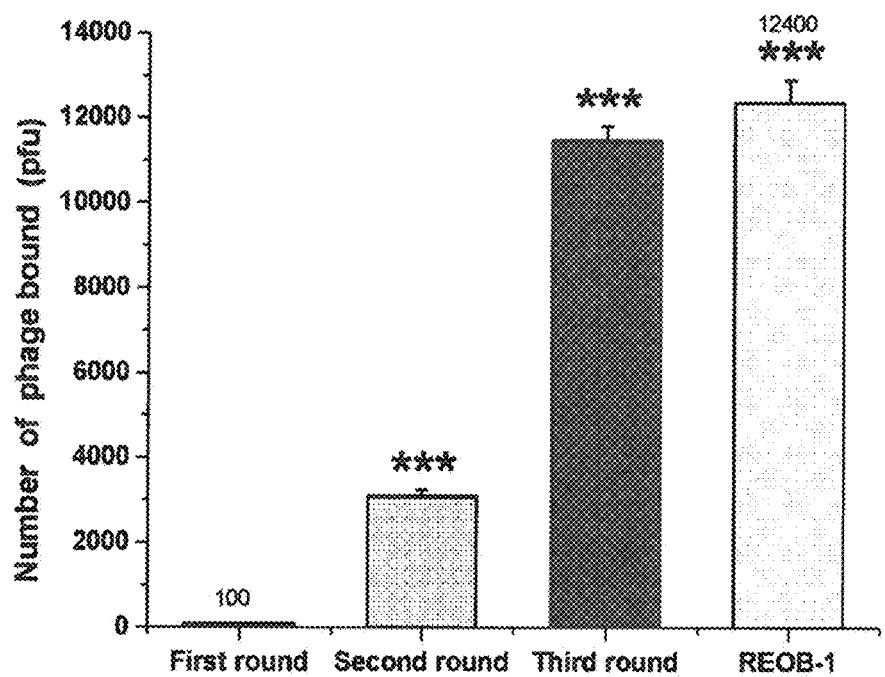
FIG. 1 is a graph showing the number of phages specifically binding to $Nd_2O_3$.
Figure 2:
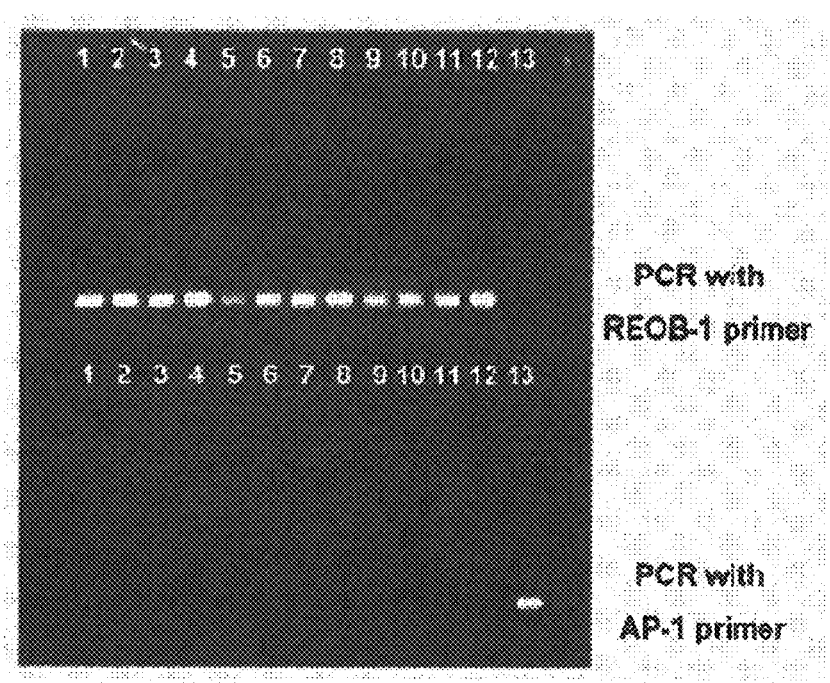
FIG. 2 is a photograph showing the results of PCR for determining the binding ability of REOB-1 phage to $Nd_2O_3$.

The present invention will be further illustrated with reference to the following specific examples. It should be understood that the following examples are only used to illustrate the present invention, but not to limit the scope thereof.

Materials and Methods:

HeLa cells used in the following examples are purchased from Institute of Biochemistry and Cell Biology, SIBS, CAS. HeLa-LC3 cells are HeLa cells stably transfected with eGFP-LC3 plasmid carrying a GFP reporter gene (provided by Prof. N. Mizushima from Tokyo Medical and Dental University, Japan). DMEM medium is purchased from Gibco (USA). UCP is purchased from Phosphor Technology (UK).

It will be appreciated by those skilled in the art that, unless otherwise indicated, the reagents, plasmids, and cells and the like used in the following examples are commercially available.

MTT cell vitality assay is performed as follows: The cells to which samples have been added are cultured for 24 hr, and then 0.5 mg/mL MTT solution is added and cultured for 4 hr. The MTT solution in the well is discharged, and then 200 µL DMSO is added, followed by gently shaking the plate on a shaking table for 10 min. Detection is performed using microplate reader (ELX800, purchased from BIO-TEK) at a wavelength of 570 nm.

PI staining assay is performed as follows: The cells to which samples have been added are cultured for 24 hr, and then to the culture Hoechst 33342 (10 mM, purchased from Sigma, USA, Catalog #: B2261) and PI (Propidium Iodide) (10 mM, purchased from Beyotime Biotechnology, Catalog #: ST511) are added for 10 min of staining. Then, the cells are detected and photographed under a fluorescence microscope (Olympus IX71, purchased from Olympus). The number of the cells counted by this assay was 500.

Western blotting is performed as follows: After an incubation of 24 h, the cells are collected and lysed with lysis buffer (purchased from Beyotime Biotechnology, China). The lysate is boiled in boiling water for 10 min, subjected to 15% SDS-PAGE, and then transferred to nylon membrane (purchased from Amersham Inc.) by a wet transfer. In the Western blotting, Anti-LC3 (Light Chain 3 Protein Antibody, purchased from Novus Inc., Catalog #: NB 100-2220) is used as primary antibody; GAPDH (purchased from Millipore Inc.) is used as internal reference; and Horseradish peroxidase (HRP) conjugated goat anti-rabbit IgG (H+L) (Goat Anti-Rabbit IgG (H+L), HRP Conjugate) (purchased from Promega Inc.) is used as secondary antibody.

Data analysis method: student's-T test was used for data analysis, and Origin software was used to draw plots.

Example 1

Screening Short Peptides Specifically Binding to $Nd_2O_3$ Using Phage Displaying Technique The phage displayed polypeptide library used to screen peptides specifically binding to $Nd_2O_3$, which was purchased from New England Biolabs (Ipswich, Mass., USA, Catalog #: E8120S), is a disulfide-containing heptapeptide library (Ph.D.-C7C). In this library, the randomized fragment is flanked by a pair of cysteine residues at both ends. They can be oxidized to form a disulfide bridge during phage assembly, resulting in a cyclized peptide, which may interact with the target. This library comprises more than $2\times10^9$ clones. Randomized peptides in the library are at the N-terminus of the small envelop protein pIII, and thus each phage particle expresses five copies. The position where the randomized sequence is expressed by phage in Ph.D.-C7C library is preceded by Ala-Cys. A short spacer (Gly-Gly-Gly-Ser) (SEQ ID NO:1) is between the randomized peptide and pIII protein. (For more details of Ph.D.™-C7C, see the manufacturer's website)

2 µL of $10^{10}$ phages were mixed with 1 mL $Nd_2O_3$ (1 mg/mL, purchased from Rare-chem Hi-tech Co. Huizhou, Guangzhou, China), incubated in shaking table at 37° C. for 2 hr, and then centrifuged at 12000 rpm for 10 min. The resulting precipitate was washed ten times with TBST (containing 2% Tween-20, pH 7.5). The phages binding to $Nd_2O_3$ were recovered, mixed with 0.5 mL of fast-growing E. coli ER2378 (New England Biolabs), and incubated for 0.5 hr. Then, to the mixture, 20 mL of LB medium (tryptone 0.2 g, yeast extract 0.1 g, NaCl 0.2 g) was added for performing an amplification for 6 hr. The phages thus amplified were resuspended in phosphate buffer (150 mM NaCl, 50 mM Tris-HCl, pH 7.5) for the second round of screening. After the first round of screening, about 100 phages were collected. The binding efficiency of the phages recovered from the third round of screening to $Nd_2O_3$ was increased by two orders of magnitude compared to the phage library (FIG. 1).

The phages recovered from the third round of screening were plated onto a LB plate containing X-gal (5-bromo-4-chloro-3-indolyl-β-D-galactoside) and IPTG (isopropyl-β-D-thiogalactoside). 15 blue plaques were randomly picked up. DNA automatic sequencer (ABI3730) was used for sequencing. The results showed that 12 of the 15 plaques comprise the same insertion sequence, encoding a peptide shown by the sequence of CTARSPWIC (RE-0, SEQ ID NO:2). That is, actually, these 12 phages represented one phage strain displaying RE-0 peptide sequence, which was designated as REOB-1. REOB-1 was used in following experiments.

Example 2

Determination of the Binding Ability of REOB-1 Phage to $Nd_2O_3$

REOB-1 phages at a titer of $10^5$ were mixed with AP-1 phages (which were randomly selected from the phage library and used as control, encoding a peptide sequence of CNATLPHQC, SEQ ID NO:32) at a titer of $10^8$, incubated with 100 µL of $Nd_2O_3$ (1 mg/mL) at 37° C. for 2 hr, and then centrifuged at 12000 rpm for 10 min. The resulting precipitate was washed ten times with TBST (containing 2% Tween-20, pH 7.5). The bound phages in the precipitate were eluted with 1 mL of 0.2 M Glycine-HCl (pH 2.2) containing 1 mg/mL BSA, and plated on a LB plate. 50 blue plaques were randomly picked, each of which was subjected to dual PCR reactions simultaneously. One used a specific primer of the REOB-1 phage (5'-CGAGGTCGCCTTG-GATTTGC-3', SEQ ID NO:33), and the other used a specific primer of the AP-1 phage (5'-GACCAGTCGCATCCGCA-GCA-3', SEQ ID NO:34). Other primers needed for the PCR reactions consist of the sequences carried by the vector, and shared by these two reactions. The PCR products were subjected to 0.8% agarose gel electrophoresis. The gel then was imaged with a gel imaging system (Tanon 1600, Tanon, China). The results showed that, although the titer of AP-1 phages added to the mixture was 1000 times greater than that of REOB-1 phages, the PCR results showed REOB-1: AP-1=12: 1, indicating that the binding ability of REOB-1 phage to Nd2O3 was 12,000 times greater than that of AP-1 phage.

Example 3

Chemical Synthesis of the Specific Binding Peptides and the Analogues Thereof The polypeptides used in the present invention were synthesized by GL Biochem (Shanghai, China) Ltd. following standard FMOC solid-phase synthesis method using a polypeptide automatic synthesizer (CS536-1381, CS Bio Co., Menlo Park, Calif., USA). The polypeptides thus synthesized were purified by HPLC to a purity of more than 95%. A mass spectrometer (ThermoFisher Scientific, Waltham, Mass., USA) was used to determine the MW of the purified polypeptides.

The peptide shown by a sequence of ACTARSPWICG (RE-1, SEQ ID NO:3) was synthesized as follows. The terminal amino acids alanine and glycine were derived from the proteins on the surface of M13. RE-1 was synthesized by standard FMOC solid-phase synthesis method. General manual synthesis procedures were as follows: About 0.2 mM Fmoc-Gly-Wang resin was added into a manual reaction tube (Peptide International), to which DMF was added to expand the resin for 2 hr. Then, 20% piperidine/DMF was added to react for 2 min to remove Fmoc protecting group. This step of removing the protecting group was repeated once. Reaction was performed on ice for 20 min. Positive results for Kaiser Assay indicated the presence of free amino groups on the resin. Amino acid residues were connected to the resin through the following recycling method: Fmoc protecting amino acids, HOBT, and DIPEA/DMF, all at an excess amount of three times greater than RE-1, were added into the reaction tube. Coupling reaction was performed for 2 hr under $N_2$ stream. The reaction tube was evacuated by a vacuum pump. The N-terminal protected peptide was washed with DMF (5×1 min) to remove excessive reactants. Then, Fmoc protecting group was removed using 20% piperidine/DMF as described above. The reaction tube was washed with DMF to remove piperidine. The same steps were repeated to couple the next amino acid in the sequence. After the side chain-protected conjugate $N^a$-Fmoc-Ala-Cys-Thr-Ala-Arg-Ser-Pro-Trp-Ile-Cys-Gly-resin (SEQ ID NO:3) was synthesized, this peptide-resin conjugate was washed with DMF (4×1 min). Then, excessive DMF was removed by use of a vacuum pump. The Fmoc protecting group at the N-terminal was removed by using 20% piperidine/DMF. The deprotection of the side chains and the cleavage of the peptide-resin bond were achieved by the treatment with 10 mL of cleaving buffer (95% trifluoroacetic acid, 2.5% water, and 2.5% triisopropylsilane) with agitation at 500 rpm for 3 hr. The resulting product was transferred into a pre-weighed conical flask, and then precipitated with ice-cold dry ether. The crude product was dried in vacuo for 48 hr. 70-100 mg crude product was purified by Reversed-Phase High-Performance Liquid Chromatography (RP-HPLC), and lyophilized into a powder. The purity of the resultant peptide was determined by analytic RP-HPLC. The molecular weight of the peptide was determined by mass spectrometry.

The control peptide ACNATLPHQCG (AP-1, SEQ ID NO:35) and the polypeptide analogues and derivatives were synthesized by the same procedures as described above. AP-1 is a peptide of 11 amino acids comprising the same terminal amino acids but irrelevant amino acids therebetween. FITC was coupled to the N-terminal of RE-1 or AP-1 via Acp.

Example 4

Determination of the Binding Ability of the Polypeptide Analogues to $Nd_2O_3$ 100 μg Nd2O3 was mixed with the polypeptides, RE-1, AP-1, RE-2, RE-3, RE-4, RE-5, RE-6, RE-7, RE-8, RE-9, RE-10, etc., respectively. To the mixture, REOB-1 phages at a titer of 108 were added. After 2 hr of incubation, the number of REOB-1 phages binding to $Nd_2O_3$ was measured. IC50 value indicated the relative activity of various polypeptides competitively inhibiting the binding of REOB-1 phages to $Nd_2O_3$ nanoparticles. The results were shown in Table 1. The polypeptide RE-1 and its analogues had different binding ability to $Nd_2O_3$.

By determining the binding ability of a variety of variants of RE-1 short peptide to rare-earth nanomaterials, the inventor further found that, there was sequence specificity in the binding of RE-1 short peptide to rare-earth nanomaterials; the two cysteine residues at the two sides of RE-1 appeared to be very important for the binding of RE-1 short peptide to $Nd_2O_3$ nanoparticles; among the 7 middle amino acids of RE-1 short peptide, threonine (T) and proline (P) appeared to be more important than the other amino acid residues. The present inventor also demonstrated that, the amino acid sequences per se of the polypeptides, rather than the order of the amino acids in the polypeptides, played a key role in the screening for peptides able to bind to inorganic nanomaterials.

TABLE 1

Binding Ability of the Polypeptide RE-1 and Its Analogs to $Nd_2O_3$

| Peptide | Sequence | IC50 (μM)* | SEQ ID NO. |
|---|---|---|---|
| RE-1 | ACTARSPWICG | 3.01 ± 0.14 | SEQ ID NO: 3 |
| AP-1 | ACNATLPHQCG | >5,000 | SEQ ID NO: 35 |
| RE-2 | TARSPWI | 1307.14 ± 6.50 | SEQ ID NO: 6 |
| RE-3 | ACWPATRISCG | 64.29 ± 2.33 | SEQ ID NO: 4 |
| RE-4 | AATARSPWICG | 270.04 ± 8.67 | SEQ ID NO: 7 |
| RE-5 | ACAARSPWICG | 688.70 ± 8.38 | SEQ ID NO: 8 |
| RE-6 | ACTAASPWICG | 78.41 ± 7.07 | SEQ ID NO: 9 |
| RE-7 | ACTARAPWICG | 83.94 ± 6.65 | SEQ ID NO: 10 |
| RE-8 | ACTARSAWICG | 439.61 ± 8.48 | SEQ ID NO: 11 |
| RE-9 | ACTARSPAICG | 86.67 ± 8.07 | SEQ ID NO: 12 |
| RE-10 | ACTARSPWACG | 71.52 ± 5.10 | SEQ ID NO: 13 |

Example 5

Inhibition of the Binding of REOB-1 to $Nd_2O_3$ by RE-1 Short Peptide

Figure 3:
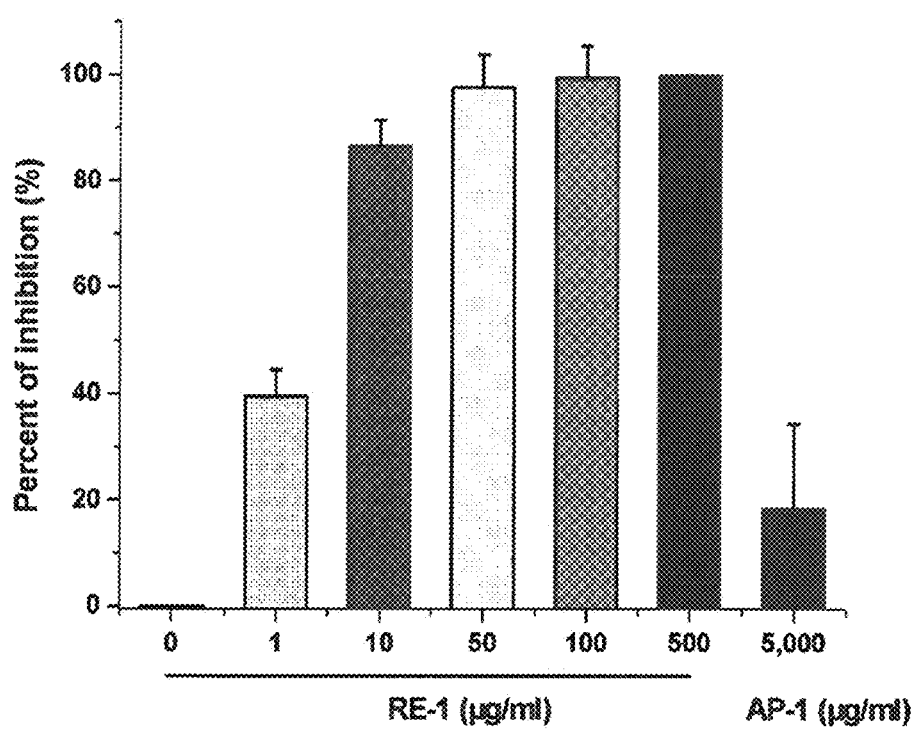
FIG. 3 is a graph showing the inhibitory effect of RE-1 peptide at various concentrations on the binding of REOB-1 phage to $Nd_2O_3$.

RE-1 short peptides at various concentrations (0 μg/mL, 1 μg/mL, 10 μg/mL, 50 μg/mL, 100 μg/mL, and 500 μg/mL) were incubated with 100 μL $Nd_2O_3$ (1 mg/mL) comprising REOB-1 phages at a titer of $10^8$ at 37° C. for 2 hr. The resulting precipitate was washed 10 times. The phages binding to $Nd_2O_3$ were recovered. 5000 μg/mL of AP-1 short peptide was treated according to the same procedure as described above, as a control. The results showed that, when RE-1 and REOB-1 were simultaneously mixed with $Nd_2O_3$, RE-1 inhibited the binding of REOB-1 to $Nd_2O_3$ in a concentration-dependent way. When the concentration is greater than 10 μg/mL, RE-1 nearly completely inhibited the binding of REOB-1 to $Nd_2O_3$ (FIG. 3). This result indicated that RE-1 short peptide appeared to be a competitive inhibitor of REOB-1 phage. The binding of REOB-1 to $Nd_2O_3$ relied on the specific interaction between the peptide displayed by the phage and the surface of the nanomaterial.

Example 6

Figure 4:
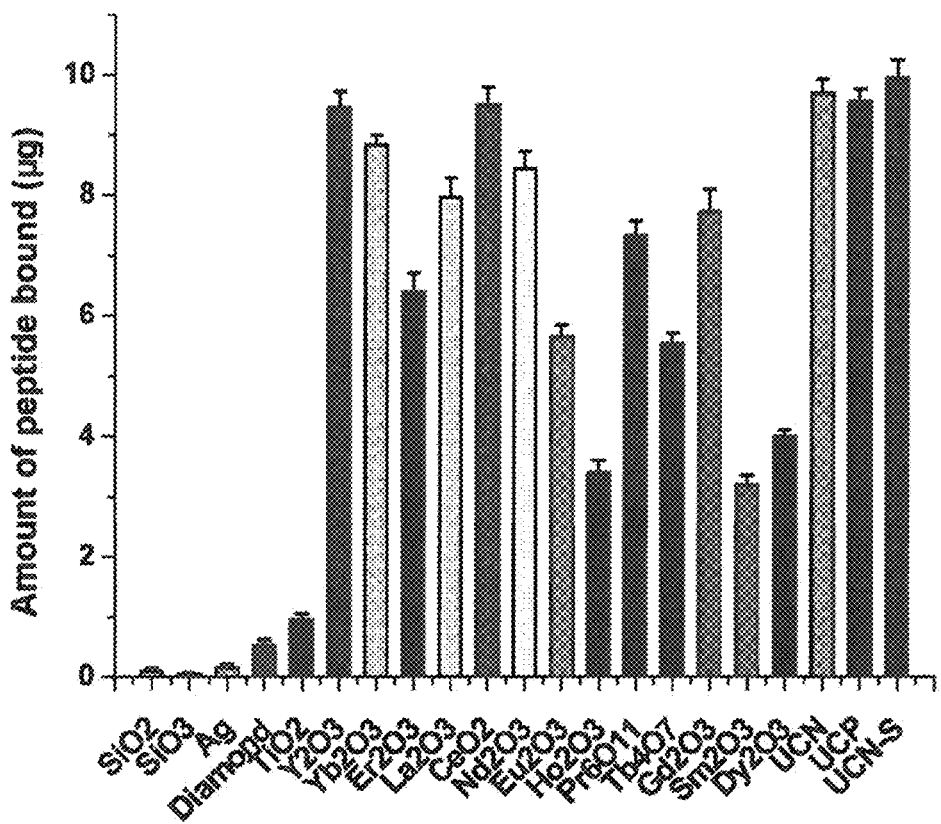
FIG. 4 is a graph showing the binding ability of RE-1 peptide to various inorganic nanomaterials.

Determination of the Binding Ability of RE-1 Short Peptide to Various Nanomaterials 10 μg of FITC-RE-1 polypeptide was incubated with 100 μL of various inorganic nanomaterials (1 mg/mL) at room temperature for 1 hr, and then centrifuged at 12000 rpm for 10 min. The resulting precipitate was washed 3 times. Then, a fluorescence spectrophotometer (RF-5301 PC, Shimadzu, Japan) was used to detect FITC (emission wavelength: 535 nm). The standard curve of fluorescence intensity vs. concentration for FITC-RE-1 was used as control, and thus the binding ability of the various inorganic nanomaterials to FITC-RE-1 polypeptide was determined. The results showed that, RE-1 strongly bound to the rare-earth upconversion nanophosphors doped with rare-earth metal oxides or rare-earth elements, most strongly for $Y_2O_3$, $CeO_2$, $Yb_2O_3$, $Nd_2O_3$, UCN (rare-earth-based upconversion nanophosphors), UCN-S (small particles of UCN), and UCP (large particles of UCN). However, RE-1 hardly bound to non rare-earth materials, such as diamond, $TiO_2$, $SiO_2$, $SiO_3$, and nano-silver (FIG. 4).

Example 7

Synthesis of UCN (NaYF4: Yb, Er)

Spherical nanoparticles of $NaYF_4$: 18% Yb, 2% Er were synthesized as follows. Yttrium chloride (0.1562 g), ytterbium chloride (0.0503 g), erbium chloride (0.0055 g), 3 mL of oleic acid, and 17 mL of octadecene were mixed in a 50-mL matrass, heated to 160° C., and then cooled to room temperature. To the matrass, a solution of sodium hydroxide (0.01 g) and ammonium fluoride (0.148 g) in methanol (10 mL) was added dropwise, stirred for 30 min for the complete reaction of the fluoride. The solution was slowly heated to evaporate methanol, degassed at 100° C. for 10 min, and then heated under argon to 300° C. and maintained for 1 hr. The solution was allowed to naturally cool down to precipitate nano-crystals. Precipitation was performed again using ethanol. The precipitate was washed 3 times with ethanol/water (1:1, vol./vol.), and treated with 1 M HCl at room temperature for 5 hr to remove oleic oil on its surface, and then washed 10 times with water and cyclohexane. The characteristic absorption peak of oleic oil at 230 nm was detected to ensure complete removal of oleic acid. UCN and UCN-S were synthesized by adding different amounts of oleic oil (UCN: 3 mL oleic acid, UCN-S: 6 mL oleic acid). The synthesized UCN was stored in water for further use.

Example 8

Observation of the Binding Form of RE-1 Short Peptide with UCN

Figure 5A:
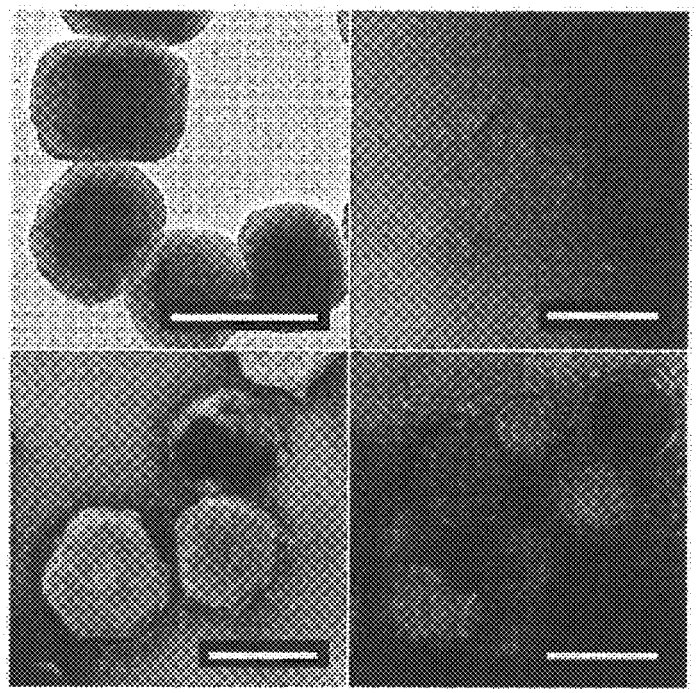
FIG. 5A, FIG. 5B, and FIG. 5C show the binding characteristics of UCN and RE-1.
Figure 5B:
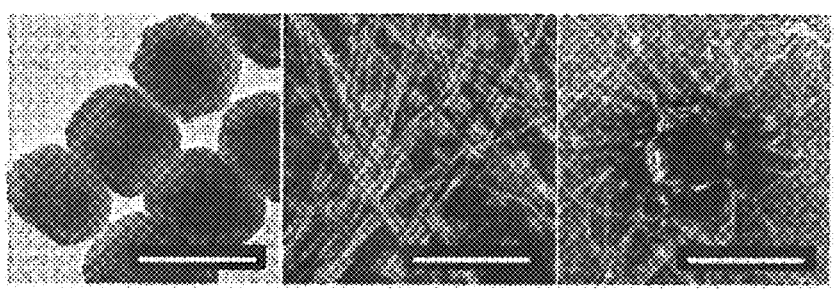

The binding forms of RE-1 short peptide and REOB-1 phage with UCN were observed using a transmission electron microscope. The excess unbound polypeptides and phages were washed off from the complex of RE-1 and UCN. The complex was stained with uranium acetate (pH 6.7), and placed on a copper mesh coated with carbon film. A transmission electron microscope TEM (200 kV) (JEM-2100F, JEOL, Japan) was used for observation and imaging (FIG. 5A and FIG. 5B).

Figure 5C:
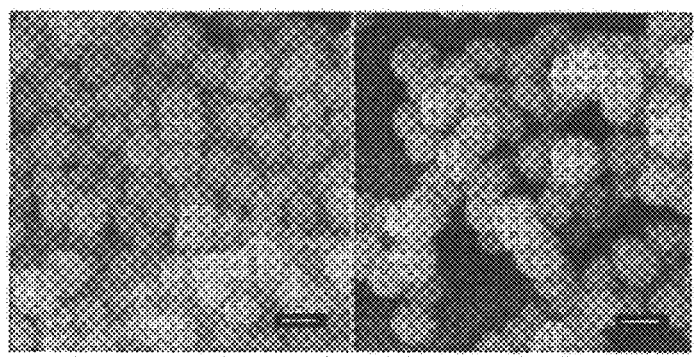

The binding form of RE-1 peptide to UCN was observed under a scanning electron microscope. The excess unbound polypeptides were washed off from the complex of RE-1 and UCN. The complex was placed on a copper mesh. A scanning electron microscope SEM (15 kV) (JEOL JSM-6700F, JEOL, Japan) was used for observation and imaging (FIG. 5C).

The results showed that REOB-1 phages were able to tightly bind to the surface of UCN with a high affinity, while the RE-1 short peptide was able to form a stable peptide coating on the surface of UCN.

Example 9

Figure 6A:
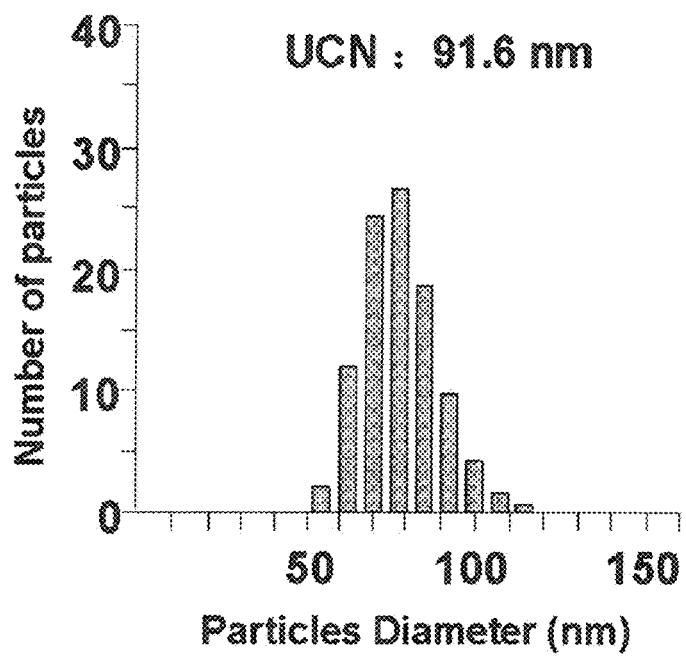
FIG. 6A, FIG. 6B, and FIG. 6C show the analysis of the particle size of rare-earth upconversion nanophosphors.
Figure 6B:
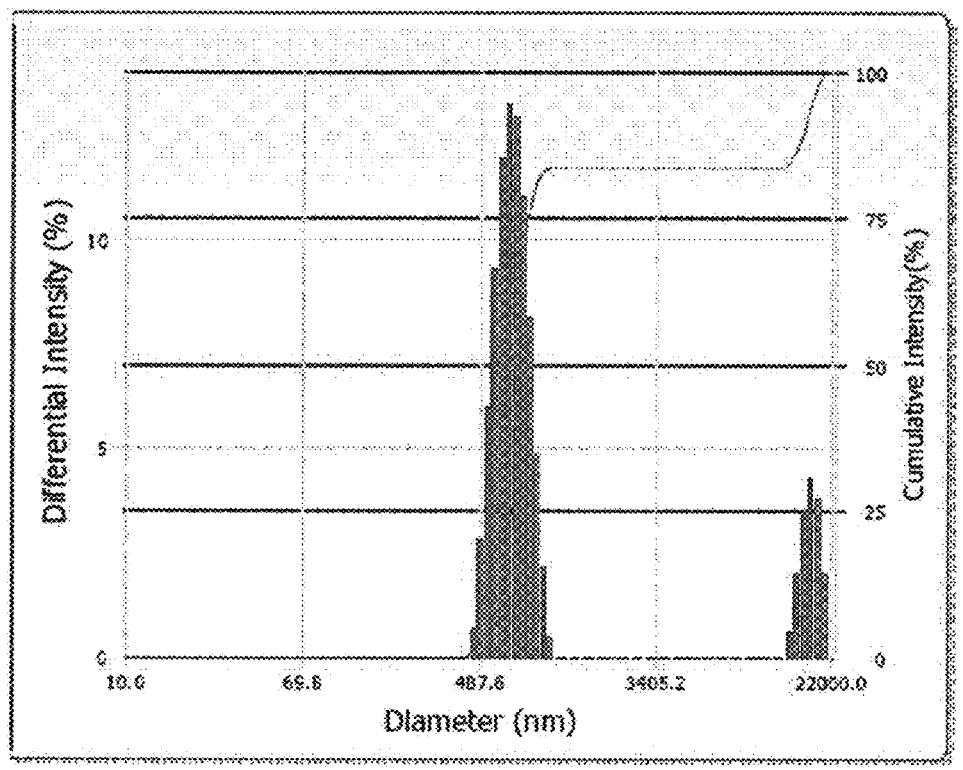
Figure 6C:
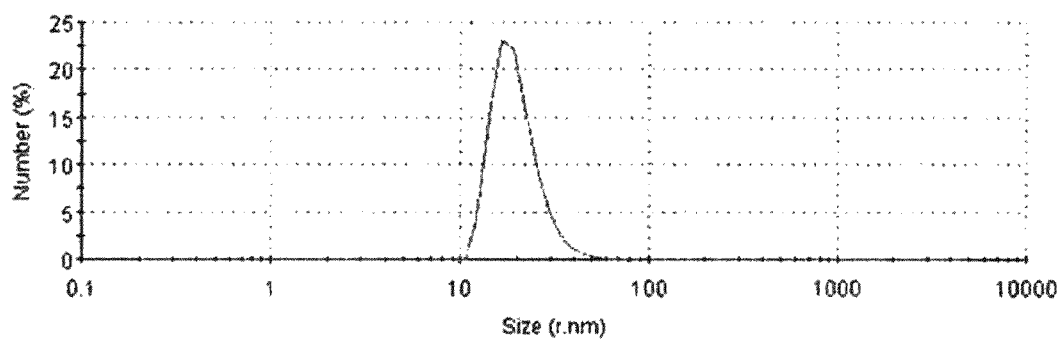

Identification of the Rare-Earth Upconversion Nanophosphors (UCN, UCP, and UCN-S) on Nanometer Scale The synthesized UCN and UCN-S as well as UCP (Phosphor Technology, UK) which is subjected to sonication and sedimentation were dissolved in water. The solution was added into a cubic cell made of polystyrene (DTS0012, Malvern, UK). The particle size distribution of the nanoparticles was measured by using Malvern Nano Laser Particle Sizer Nano ZS90 (Malvern, UK) equipped with 633 nm helium/neon laser. The results showed that the particle size of UCN was about 92 nm (FIG. 6A), the particle size of UCP was about 500 nm (FIG. 6B), and the particle size of UCN-S was about 20 nm (FIG. 6C).

Example 10

Measurement of the Binding Ability of RE-1 Short Peptide to the Rare-Earth Upconversion Nanophosphors (UCN, UCP, and UCN-S)

Figure 7A:
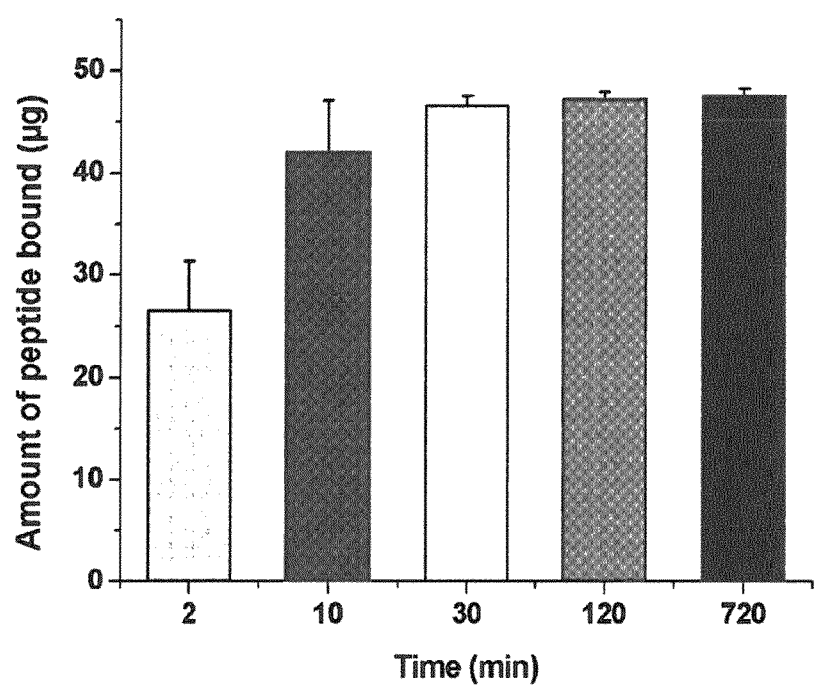
FIG. 7A, FIG. 7B, FIG. 7C, FIG. 7D, and FIG. 7E show the binding curve of rare-earth upconversion nanophosphors to RE-1.

50 μg of FITC-RE-1 was incubated with 100 μg of UCN for different time periods (2 min, 10 min, 30 min, 120 min, and 720 min). Then, the amount of FITC-RE-1 fluorescent peptide binding to UCN was measured by using fluorescence spectrophotometer. The results showed that RE-1 rapidly bound to UCN, 50% binding at 2 min, and almost binding saturation at 10 min (FIG. 7A).

Figure 7B:
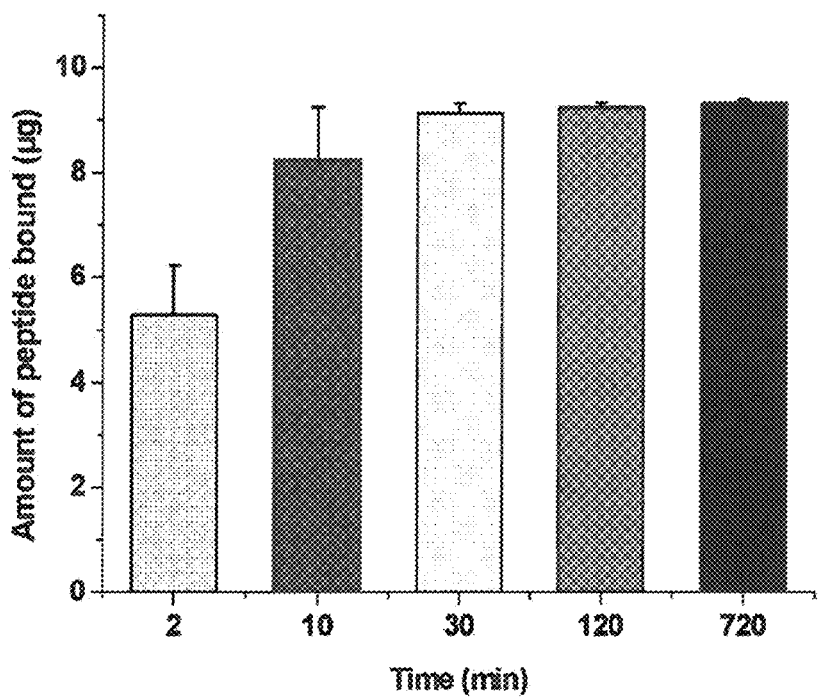

10 μg of FITC-RE-1 was incubated with 100 μg of UCP for different time periods (2 min, 10 min, 30 min, 120 min, and 720 min). Then, the amount of FITC-RE-1 fluorescent peptide binding to UCP was measured by using fluorescence spectrophotometer. The results showed that, the binding of RE-1 to UCP also had a time-dynamics distribution: likewise, 50% binding occurred at 2 min, and almost binding saturation occurred at 10 min (FIG. 7B).

Figure 7C:
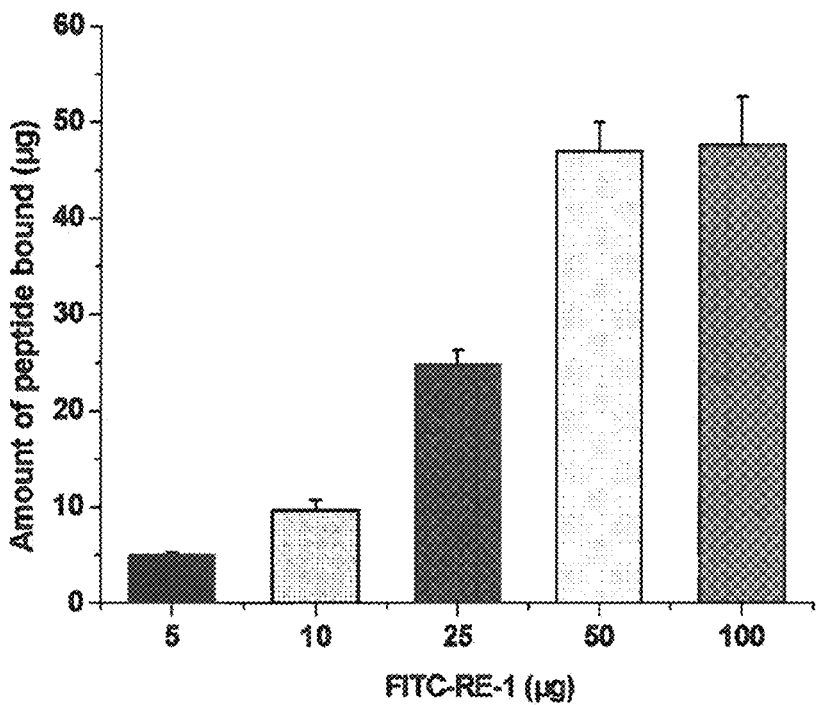

100 μg of UCN was incubated with FITC-RE-1 at various concentrations (5 μg, 10 μg, 25 μg, 50 μg, and 100 μg) for 1 hr. The excess and unbound peptides were washed off. The amount of FITC-RE-1 fluorescent peptide binding to UCN was measured by using fluorescence spectrophotometer. The results showed that 100 μg of UCN was able to bind 47 μg of FITC-RE-1 (FIG. 7C).

Figure 7D:
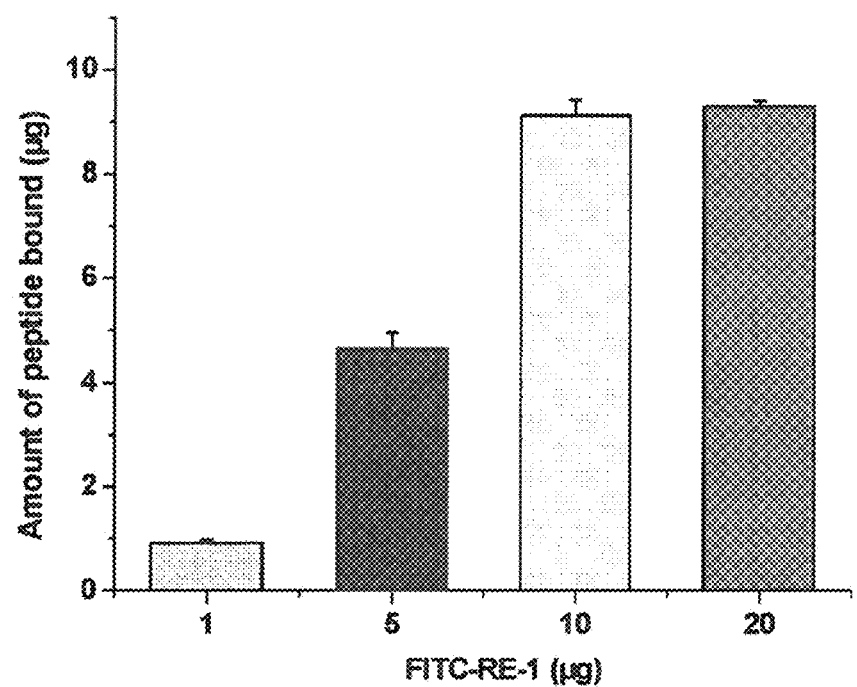

100 μg of UCP was incubated with FITC-RE-1 at various concentrations (1 μg, 5 μg, 10 μg, and 20 μg) for 1 hr. The excess and unbound peptides were washed off. The amount of FITC-RE-1 fluorescent peptide binding to UCP was measured by using fluorescence spectrophotometer. The results showed that 20 μg of UCP was able to bind 9.2 μg of FITC-RE-1 (FIG. 7D).

Figure 7E:
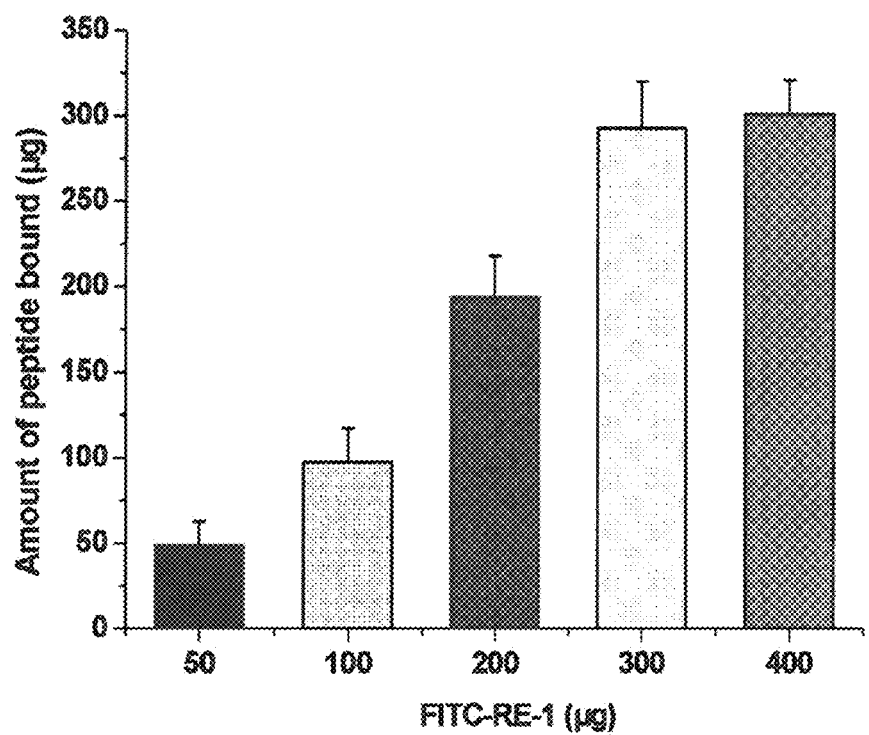

100 μg of UCN-S was incubated with FITC-RE-1 at various concentrations (50 μg, 100 μg, 200 μg, 300 μg, and 400 μg) for 1 hr. The excess and unbound peptides were washed off. The amount of FITC-RE-1 fluorescent peptide binding to UCN-S was measured by using fluorescence spectrophotometer. The results showed that, 400 μg of UCN-S was able to bind with 301 μg of FITC-RE-1 (FIG. 7E).

Example 11

The Effect of Solution Conditions on the Binding Ability of RE-1 Short Peptide to the Rare-Earth Upconversion Nanophosphors (UCN, UCP)

Figure 8A:
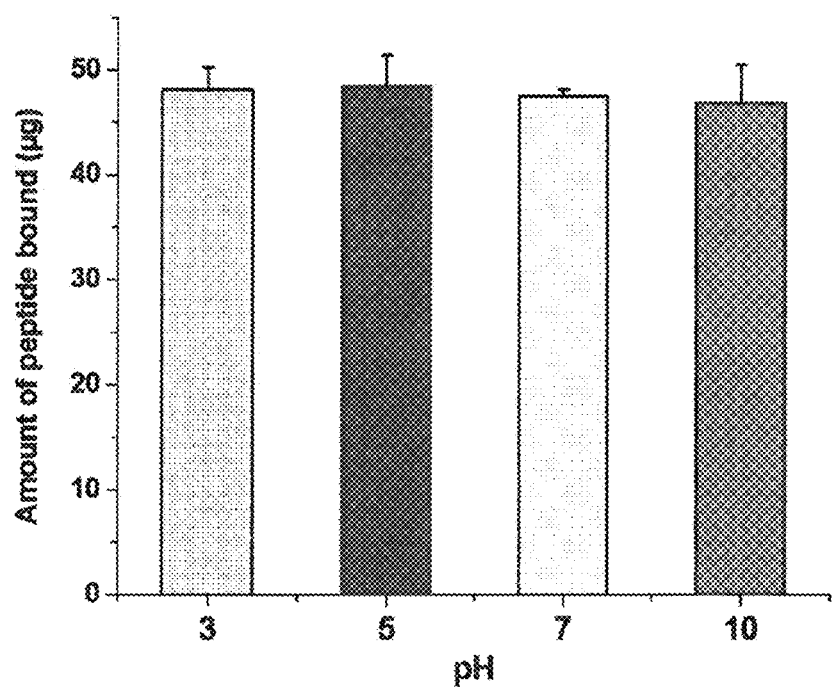
FIG. 8A, FIG. 8B, FIG. 8C, FIG. 8D, FIG. 8E, and FIG. 8F show the effect of environment on the binding of rare-earth upconversion nanophosphors to RE-1.

50 μg of FITC-RE-1 was incubated with 100 μg of UCN dissolved at different pH values (pH 3, 5, 7, and 10) for 1 hr. The excess and unbound peptides were washed off. The amount of FITC-RE-1 fluorescent peptide binding to UCN was measured by using fluorescence spectrophotometer. The results showed that, the binding of FITC-RE-1 to UCN was not susceptible to the pH of the solution (FIG. 8A).

Figure 8B:
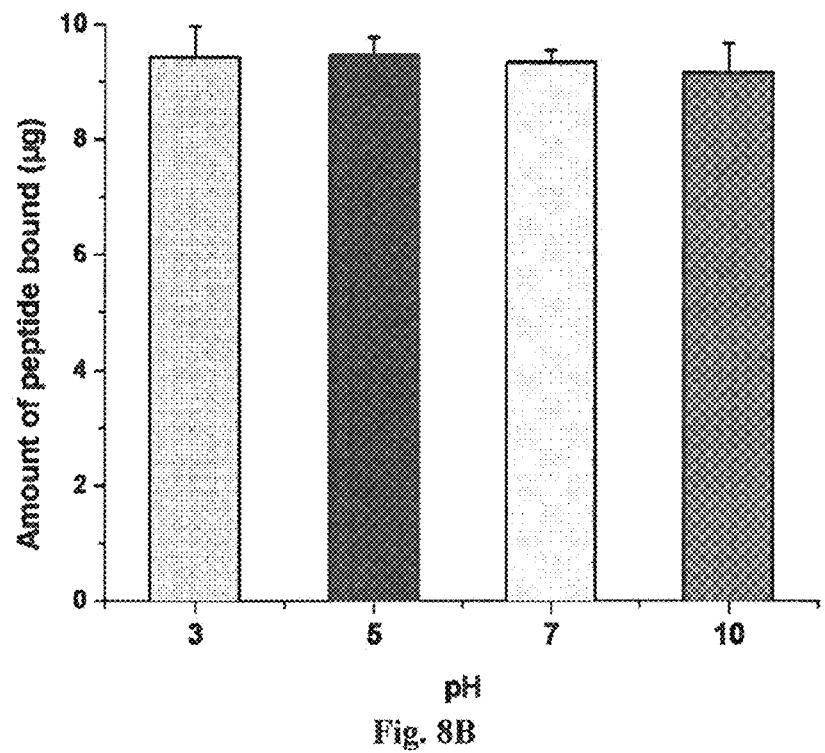

10 μg of FITC-RE-1 was incubated with 100 μg of UCP dissolved at different pH values (pH 3, 5, 7, 10) for 1 hr. The excess and unbound peptides were washed off. The amount of FITC-RE-1 fluorescent peptide binding to UCP was measured by using fluorescence spectrophotometer. The results showed that, the binding of FITC-RE-1 to UCP was not susceptible to the pH of the solution (FIG. 8B).

Figure 8C:
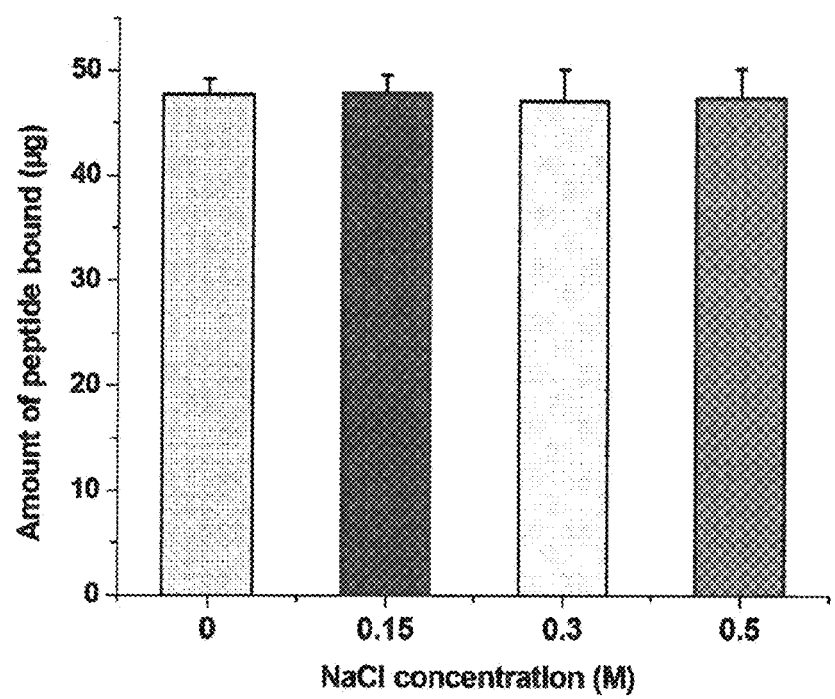

50 μg of FITC-RE-1 was incubated with 100 μg of UCN dissolved at different salt ion concentrations (0 M, 0.15 M, 0.3 M, and 0.5 M NaCl) for 1 hr. The excess and unbound peptides were washed off. The amount of FITC-RE-1 fluorescent peptide binding to UCN was measured by using fluorescence spectrophotometer. The results showed that, the binding of FITC-RE-1 to UCN was not susceptible to salt ion concentrations (FIG. 8C).

Figure 8D:
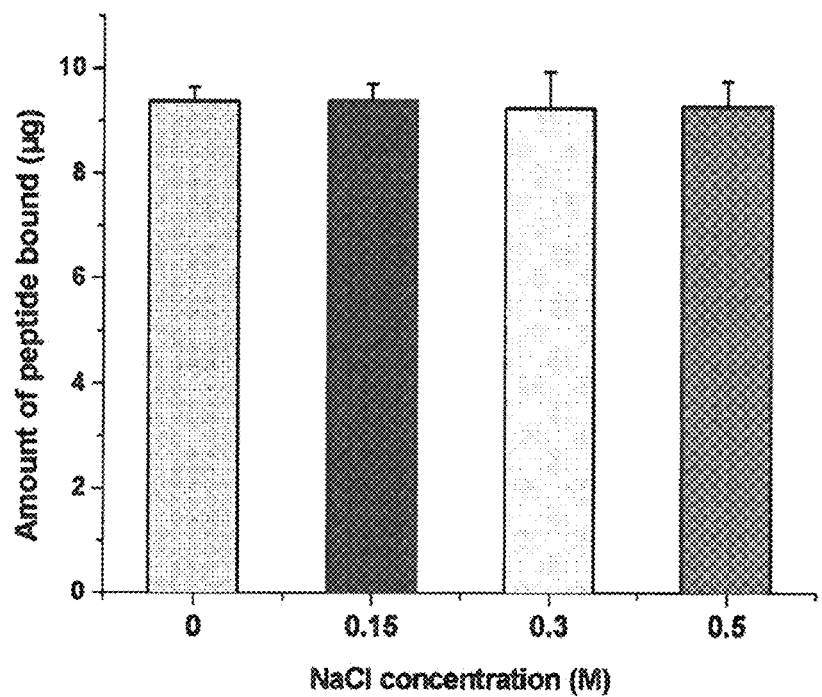

10 μg of FITC-RE-1 was incubated with 100 μg of UCP dissolved at different salt ion concentrations (0 M, 0.15 M, 0.3 M, and 0.5 M NaCl) for 1 hr. The excess and unbound peptides were washed off. The amount of FITC-RE-1 fluorescent peptide binding to UCP was measured by using fluorescence spectrophotometer. The results showed that, the binding of FITC-RE-1 to UCP was not susceptible to salt ion concentrations (FIG. 8D).

Figure 8E:
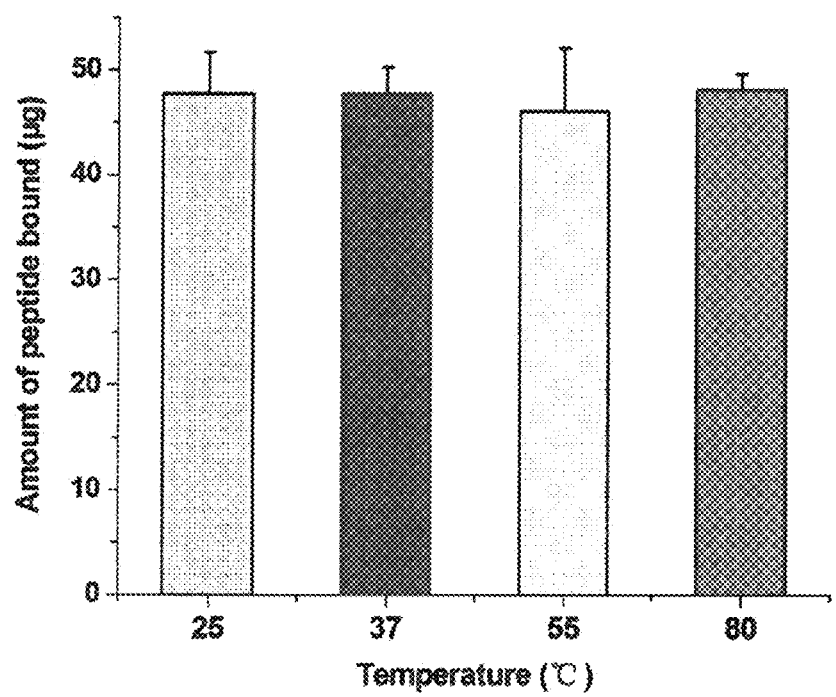

50 μg of FITC-RE-1 was incubated with 100 μg of UCN dissolved in water at different temperatures (25° C., 37° C., 55° C., and 80° C.) for 1 hr. The excess and unbound peptides were washed off. The amount of FITC-RE-1 fluorescent peptide binding to UCN was measured by using fluorescence spectrophotometer. The results showed that, the binding of FITC-RE-1 to UCN was not susceptible to temperature (FIG. 8E).

Figure 8F:
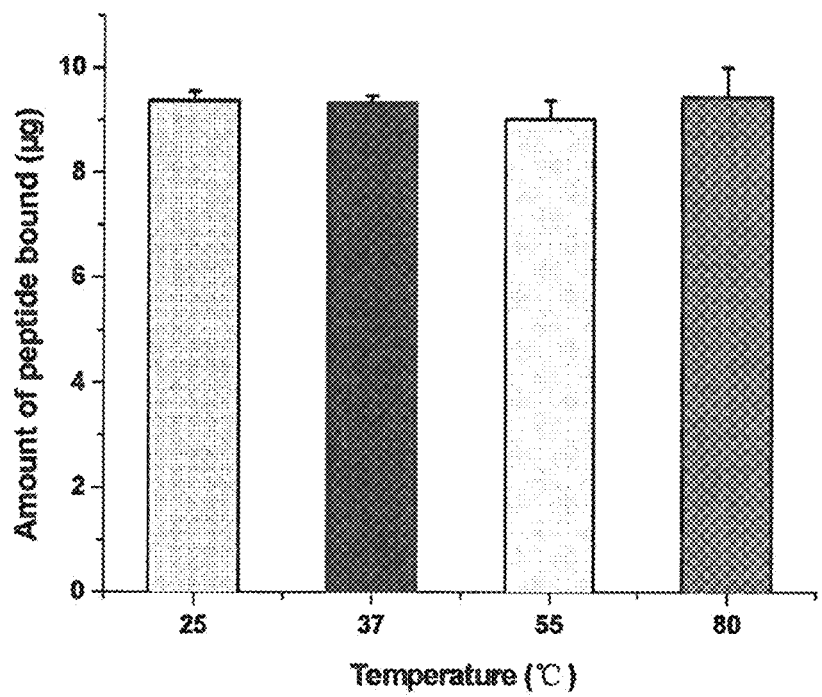

10 μg of FITC-RE-1 was incubated with 100 μg of UCP dissolved in water at different temperatures (25° C., 37° C., 55° C., and 80° C.) for 1 hr. The excess and unbound peptides were washed off. The amount of FITC-RE-1 fluorescent peptide binding to UCP was measured by using fluorescence spectrophotometer. The results showed that, the binding of FITC-RE-1 to UCP was not susceptible to temperature (FIG. 8F).

To sum up, there was a strong binding between RE-1 and the rare-earth upconversion nanophosphors (UCN, UCP), and their binding was not destroyed by the change of the environmental conditions.

Example 12

Determination of the Dissociation of RE-1 Short Peptide and Rare-Earth Upconversion Nanophosphors (UCN, UCP)

Figure 9A:
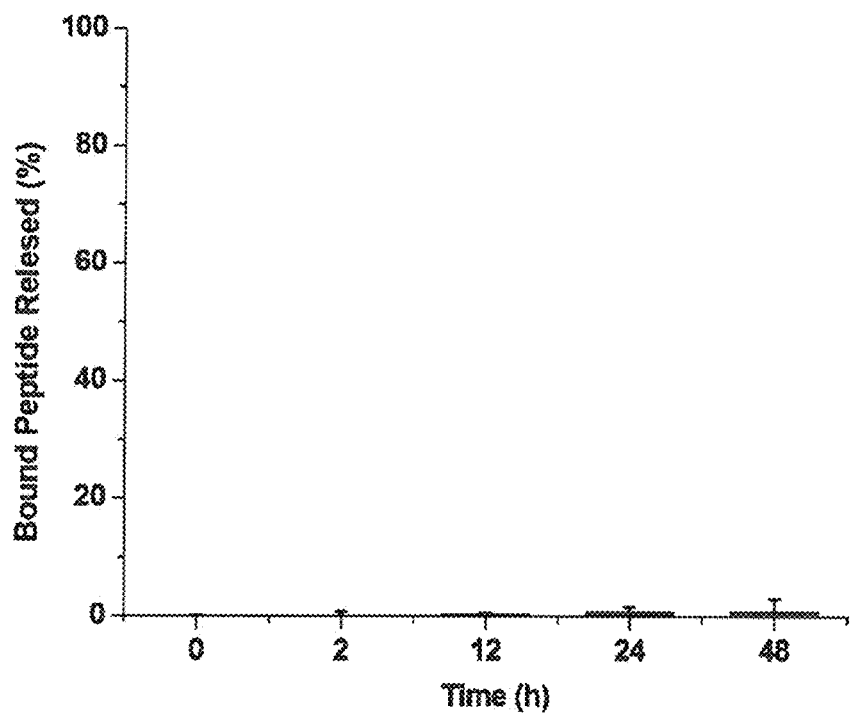
FIG. 9A and FIG. 9B show the dissociation of RE-1 from rare-earth upconversion nanophosphors after binding over time.

250 μg FITC-RE-1 was thoroughly mixed with 500 μg UCN. The excess and unbound polypeptides were washed off. Then, the mixture was divided into five aliquots. The aliquots were gently shaked on a shaking table at 37° C. The amount of FITC-RE-1 dissociated in the supernatants was measured by using a fluorescence spectrophotometer at different time points (0 hr, 2 hr, 12 hr, 24 hr, and 48 hr). The results showed that, RE-1 was stably bound to UCN, with a dissociation of only less than 0.7% after 48 h (FIG. 9A).

Figure 9B:
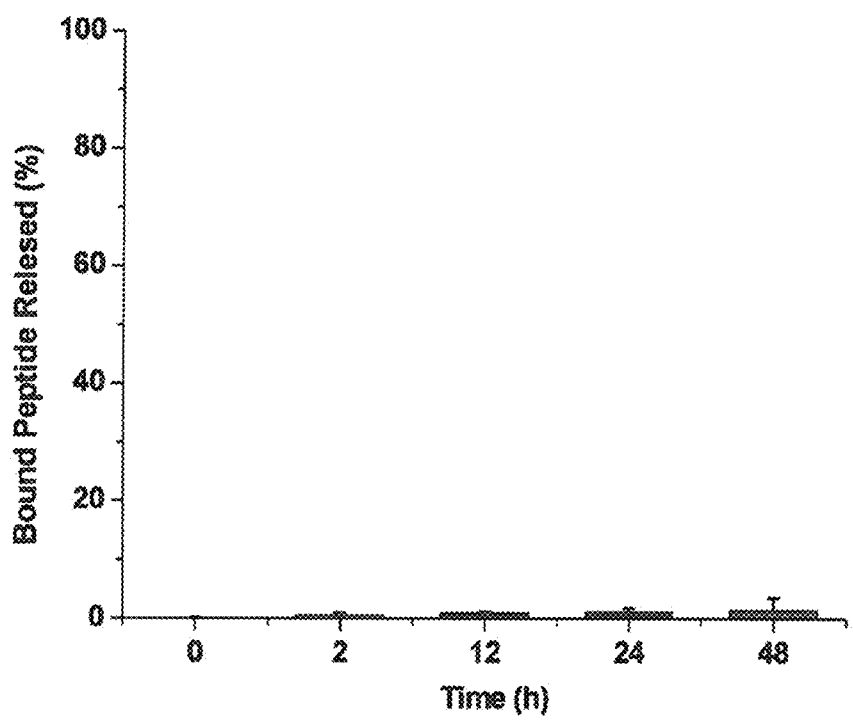

The process described above was repeated except that 50 μg FITC-RE-1 and 500 μg UCP were used. The amount of FITC-RE-1 dissociated in the supernatants was measured. The results showed that, RE-1 was stably bound to UCP, with a dissociation of only less than 1.5% after 48 hr (FIG. 9B).

Example 13

RE-1 Reduced the Sedimentation Rate of the Rare-Earth Upconversion Nanophosphors (UCN, UCP)

Figure 10A:
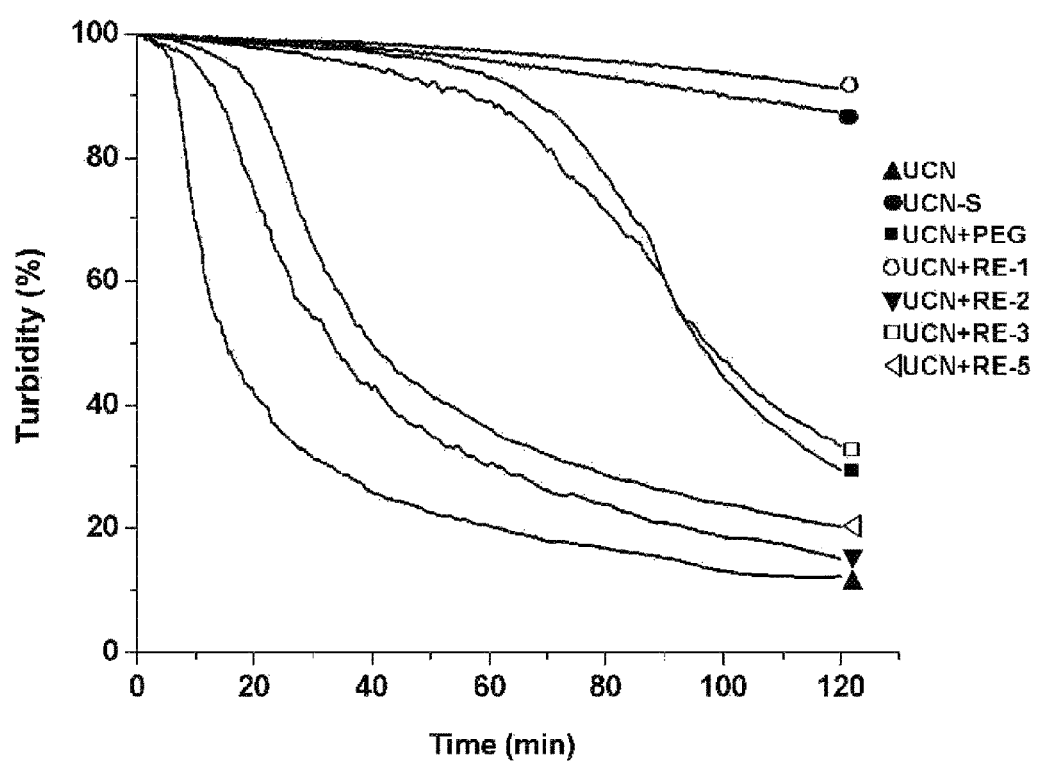
FIG. 10A and FIG. 10B are time-dynamics curves showing that RE-1 improved the suspension ability of rare-earth upconversion nanophosphors.

3 mg of UCN was mixed with 1.5 mg of RE-1 or its analogues RE-2, RE-3, or RE-5 as well as PEG, and the binding between them was performed according to a binding method. The excess and unbound RE-1 was washed off. The resultant precipitate was resuspended in 3 mL water, sonicated for 1 min, and then placed into a UV detection cell (X72053, Alpha Laboratories Ltd, UK). Observation was made using a UV spectrophotometer (DU-640, Beckman, USA) at an absorption wavelength of 500 nm for 120 min to obtain a time-dynamics curve. The results showed that, UCN without RE-1 coating rapidly sedimented at the bottom of the cell, while UCN coated with RE-1 short peptide was still in suspension after standing for 120 min, indicating that RE-1 effectively reduced the sedimentation rate of UCN (FIG. 10A).

Figure 10B:
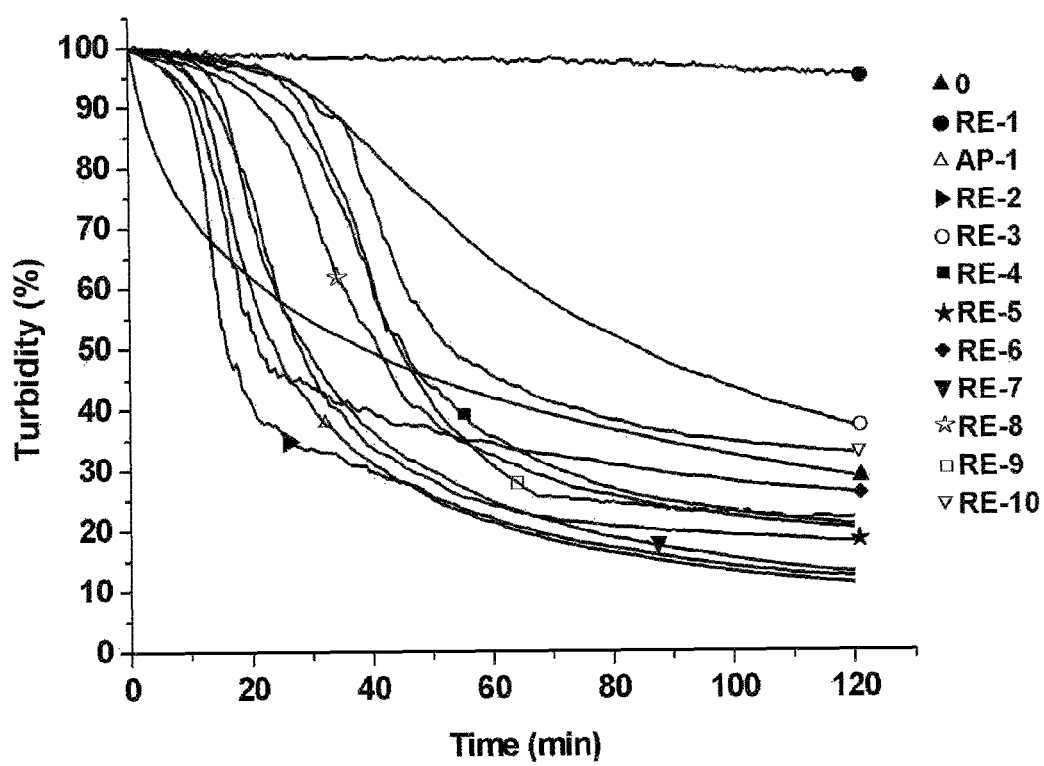

The process described above was repeated except that 3 mg UCP and 500 μg RE-1 or its analogues RE-2, RE-3, RE-4, RE-5, RE-6, RE-7, RE-8, RE-9, or RE-10 and AP-1 were used. A time-dynamics curve was obtained. The results showed that, UCP without RE-1 coating rapidly sedimentated at the bottom of the cell, while UCP bound with RE-1 short peptide was still in suspension after standing for 120 min, indicating that RE-1 effectively reduced the sedimentation rate of UCP (FIG. 10B).

Example 14

RE-1 Reduced Nonspecific Adherence of the Rare-Earth Upconversion Nanophosphors (UCN, UCN-S)

Figure 11A:
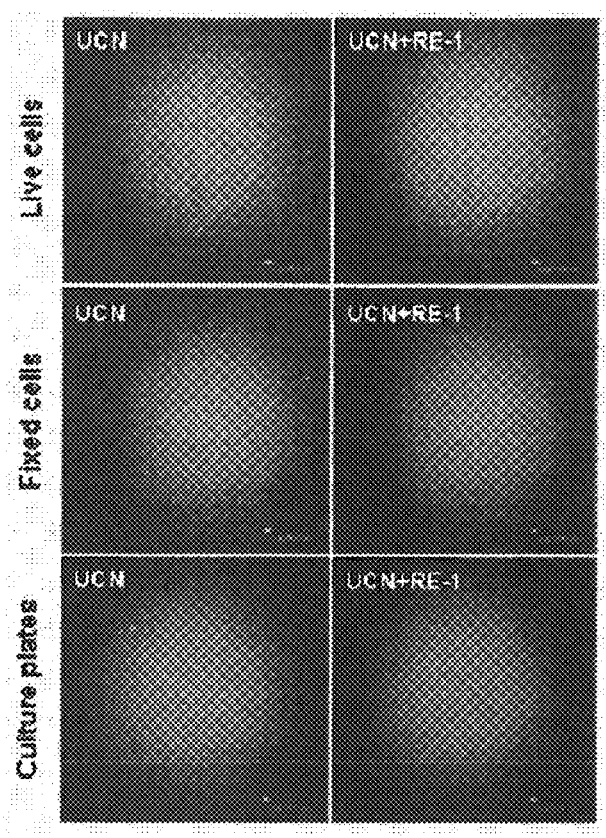
FIG. 11A, FIG. 11B, FIG. 11C, and FIG. 11D show that RE-1 reduced nonspecific adherence of rare-earth upconversion nanophosphors.
Figure 11B:
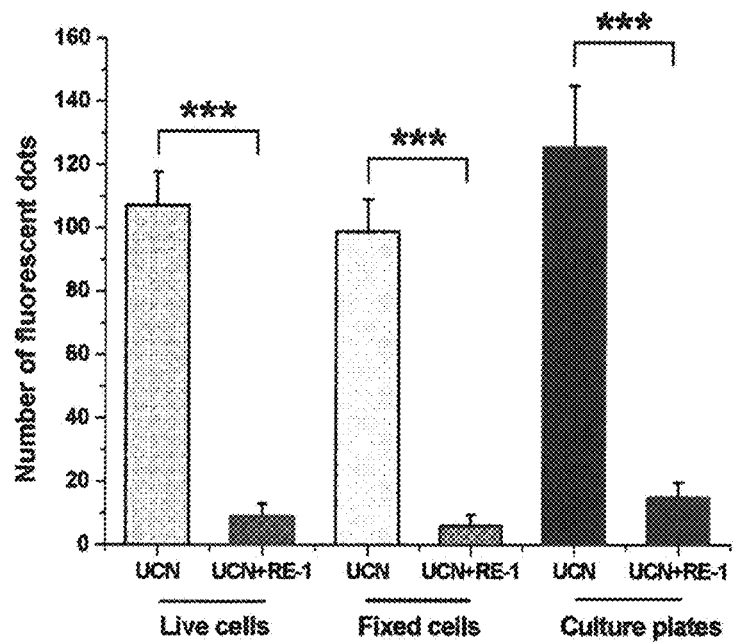
Figure 11C:
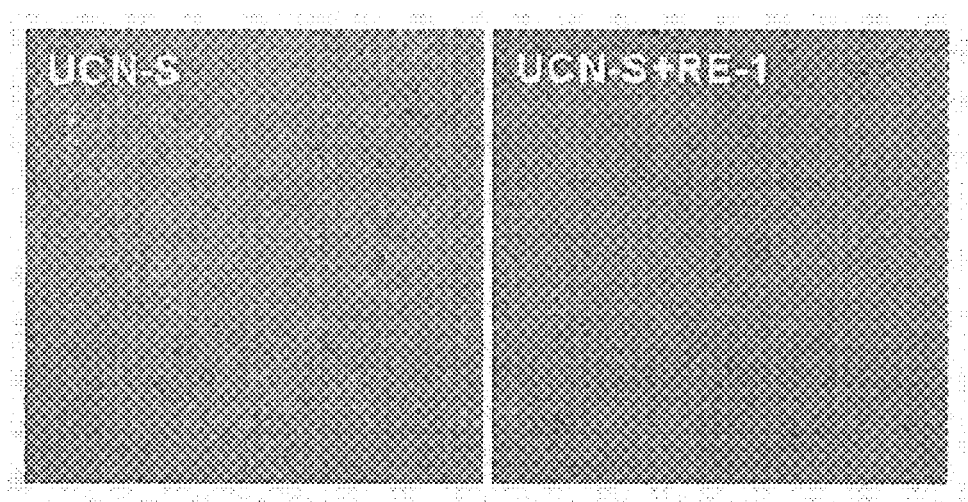
Figure 11D:
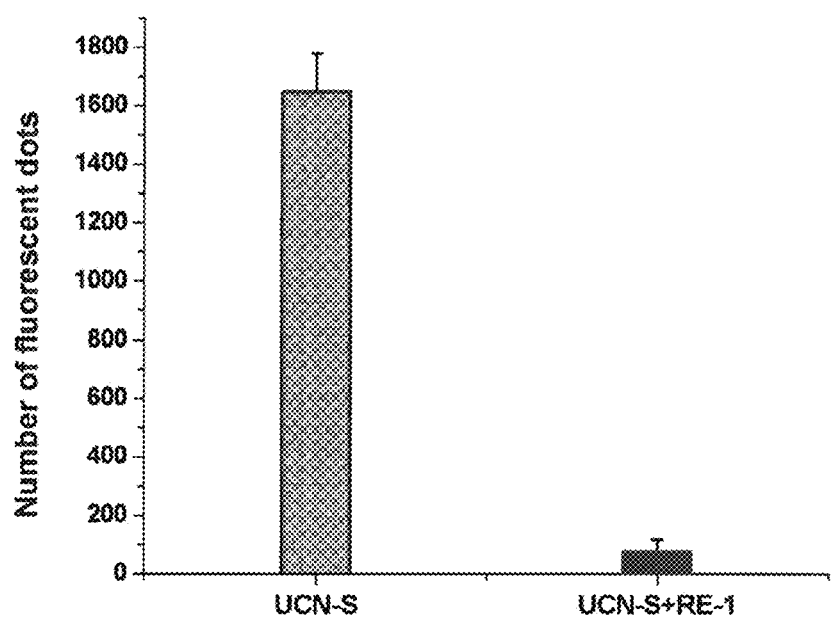

Living HeLa cells (purchased from Institute of Biochemistry and Cell Biology, SIBS, CAS) cultured in a 96-well plate, immobilized cells, and cell culturing plate were treated with UCN and UCN-S with or without RE-1 coating for 2 hr, respectively, and then washed with PBS for 3 times. The binding of UCN nanoparticles to the living HeLa cells, the immobilized cells, and the cell culturing plate was observed under a fluorescence microscope (Olympus IX71, Olympus, Japan) equipped with a 980 nm infrared laser (MDL-980 nm 1W, Changchun New Industries Optoelectronics Tech. Co., Ltd, China). The results showed that, the nonspecific adherence of the UCN coated with RE-1 to the living HeLa cells, the immobilized cells, and the cell culturing plate was about 10 times lower than that of the UCN without RE-1 coating (FIG. 11A and FIG. 11B); the nonspecific adherence of the UCN-S coated with RE-1 to the living HeLa cells, the immobilized cells, and the cell culturing plate was about 100 times lower than that of the UCN-S without RE-1 coating (FIG. 11C and FIG. 11D).

Example 15

Figure 12A:
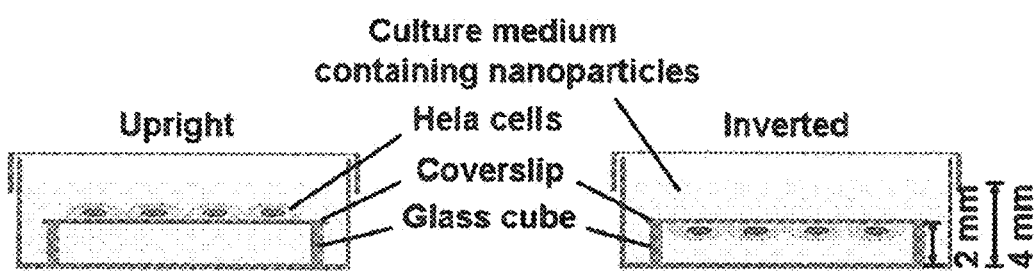
FIG. 12A, FIG. 12B, FIG. 12C, FIG. 12D, FIG. 12E, FIG. 12F, FIG. 12G, and FIG. 12H show that RE-1 reduced the diffusibility of rare-earth upconversion nanophosphors in solution.
Figure 12B:
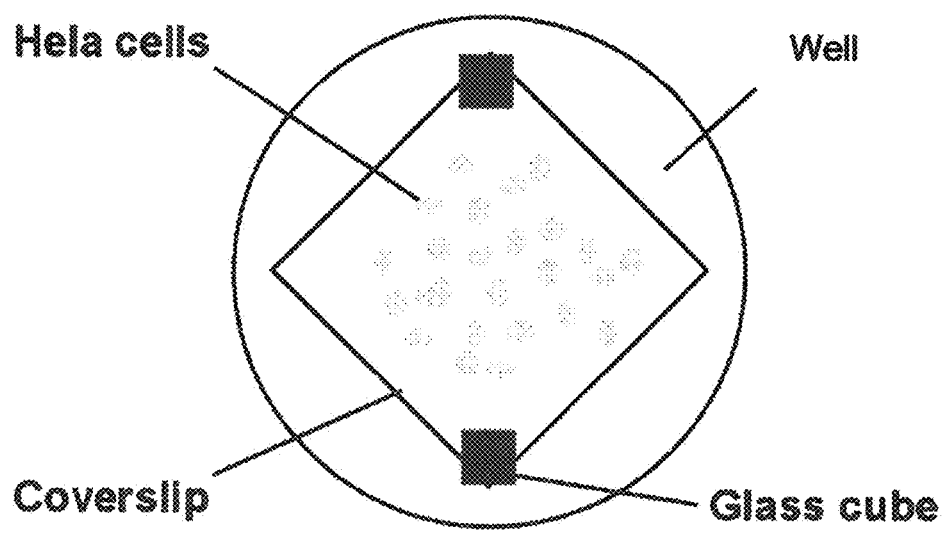
Figure 12C:
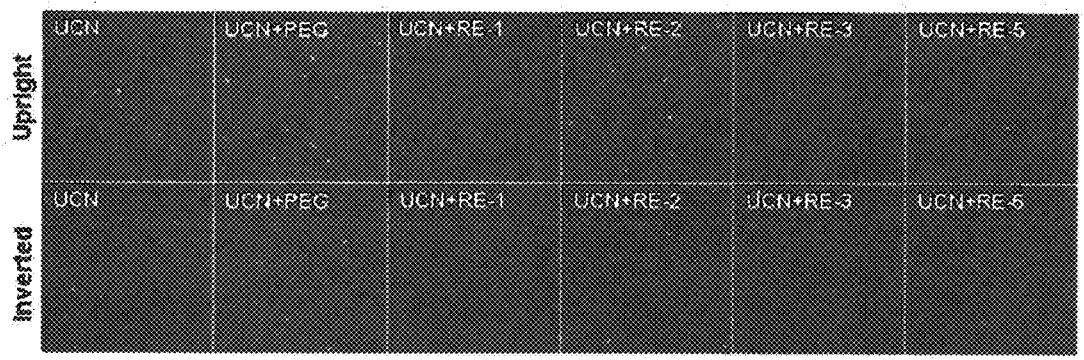
Figure 12D:
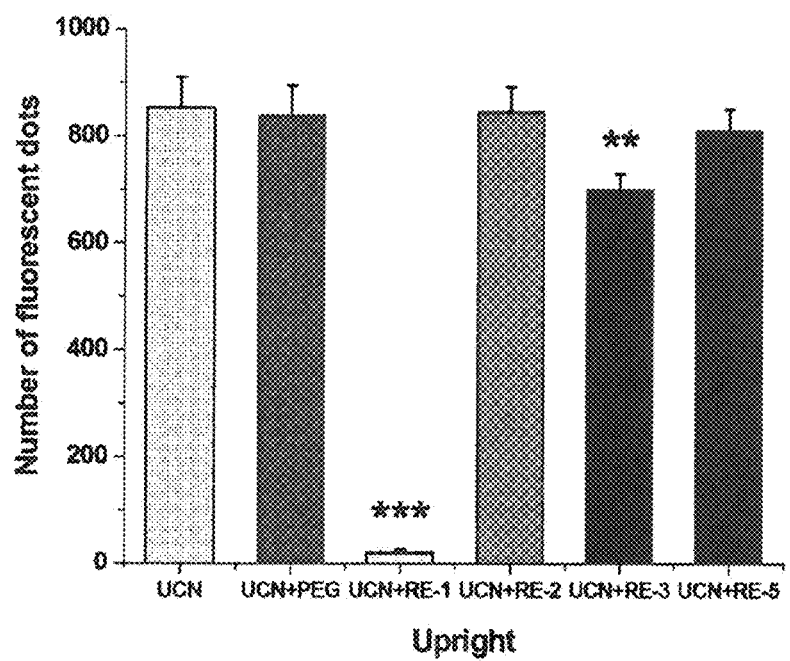
Figure 12E:
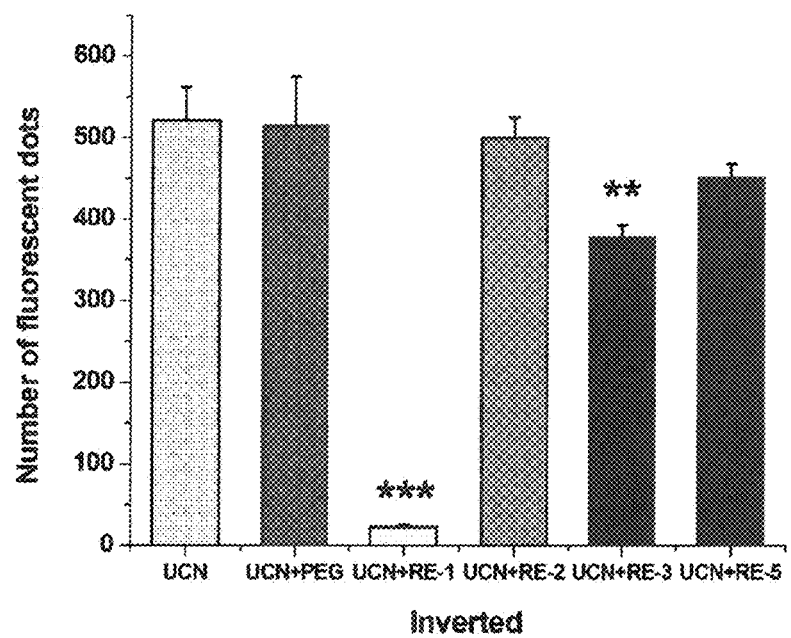
Figure 12F:
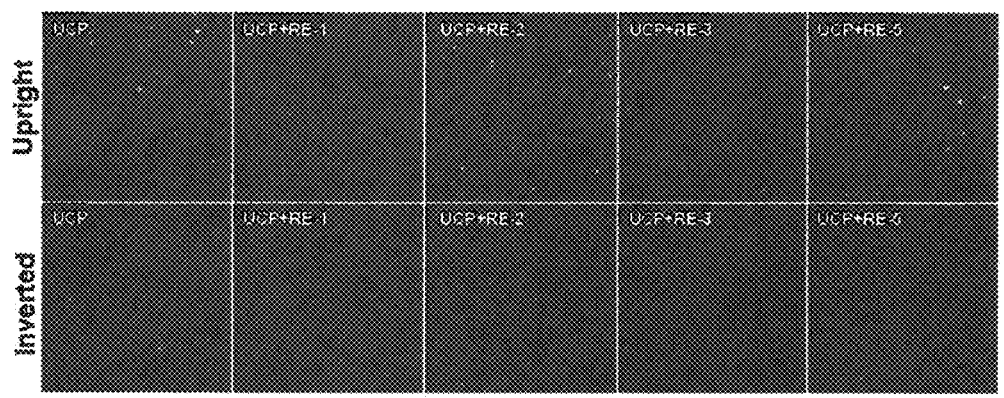
Figure 12G:
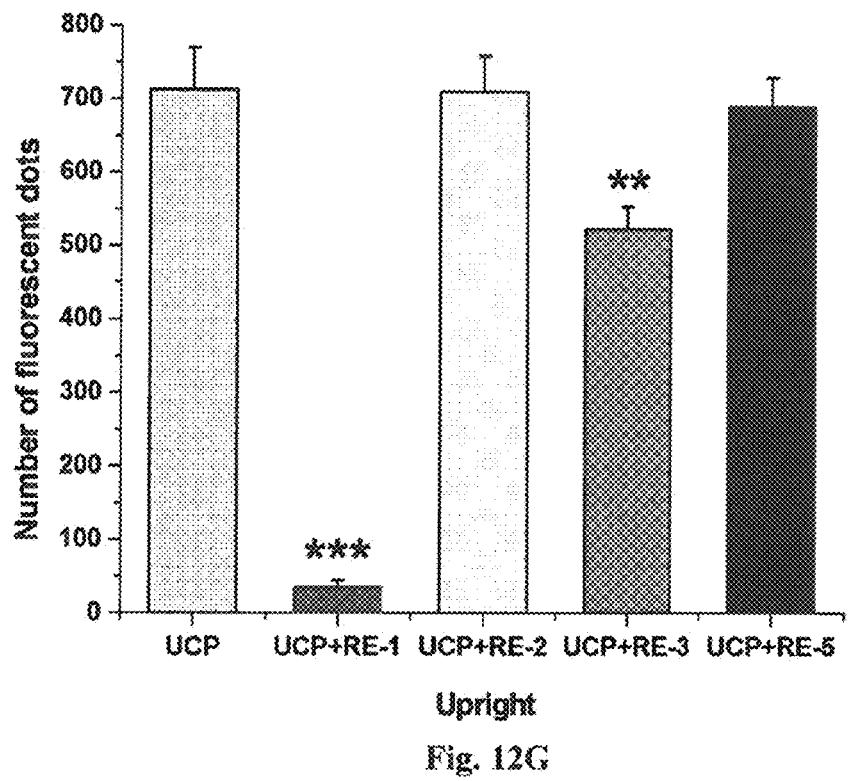
Figure 12H:
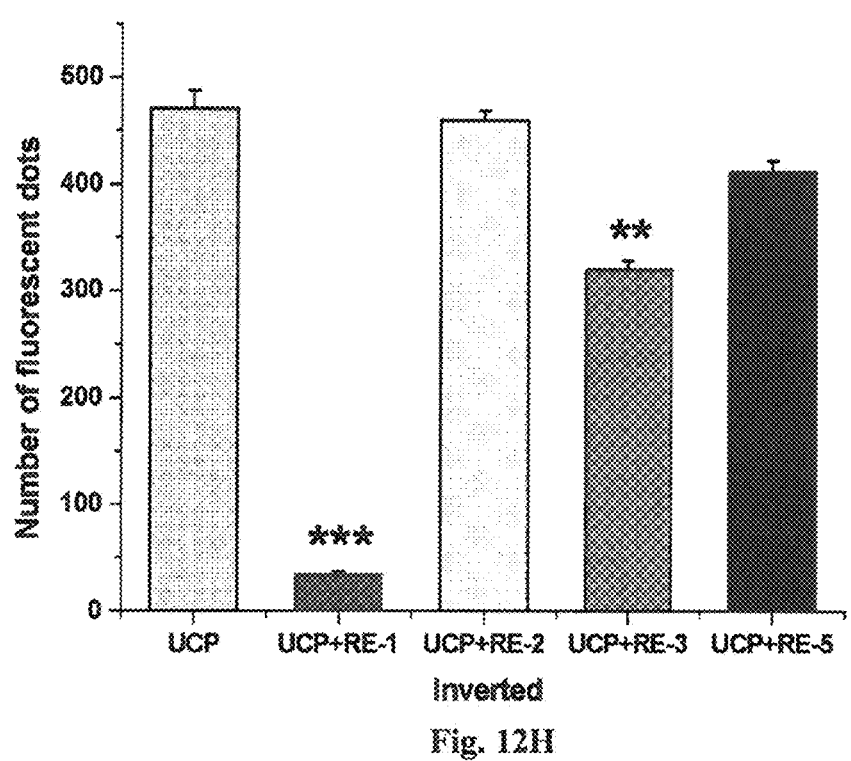

RE-1 Reduced the Diffusibility of the Rare-Earth Upconversion Nanophosphors (UCN, UCP) in Solution HeLa cells were cultured on a coverslip (22 mm×22 mm), which was then placed into a 6-well plate with the cells facing upward or downward, and the coverslip was supported by a sterilized glass cube (2 mm×2 mm×2 mm). Then, 4 mL DMEM medium (Gibco) containing the rare-earth upconversion nanophosphors (UCN, UCP) with or without RE-1 coating was slowly poured into the 6-well plate, such that the cells were fully immersed in the medium, and the coverslip is just located at the middle of the height of the liquid. The cells were placed into a cell incubator at 37° C. for 2 hr, and then washed with PBS 3 times. The UCNs adhered to the surfaces of the cells were observed under a fluorescence microscope (Olympus IX71, Olympus, Japan) equipped with a 980-nm infrared laser (MDL-980 nm 1 W, Changchun New Industries Optoelectronics Tech. Co., Ltd, China). The results showed that, for the cell-facing-upward experiment group, the rare-earth upconversion nanophosphors without RE-1 coating nonspecifically adhered to the cell surfaces at a large amount, while the amount of the rare-earth upconversion nanophosphors coated with RE-1 adhered to the cell surfaces was significantly reduced. The nonspecific adherence of the rare-earth upconversion nanophosphors without RE-1 coating to the cell surface was slightly reduced for the cell-facing-downward experiment group relative to that for the cell-facing-upward experiment group, but was still much more than that of the rare-earth upconversion nanophosphors coated with RE-1. These results indicated that RE-1 not only reduced the sedimentation rates of UCN and UCP, but also reduced the diffusibility of the rare-earth upconversion nanophosphors, thereby reducing the nonspecific adherence of the rare-earth upconversion nanophosphors (FIG. 12A and FIG. 12B are schematic views of experimental device, FIG. 12C, FIG. 12D and FIG. 12E show the results for UCN, and FIG. 12F, FIG. 12G and FIG. 12H show the results for UCP).

Example 16

The Ability of the Rare-Earth Upconversion Nanophosphors (UCN, UCP, UCN-S) as Autophagy Inducers to Induce Cell Autophagy Example 16

The Ability of the Rare-Earth Upconversion Nanophosphors (UCN, UCP, UCN-S) as Autophagy Inducers to Induce Cell Autophagy HeLa-LC3 cells were inoculated into a 96-well cell culturing plate at a density of about $1$-$2\times10^4$ cells/well, and cultured overnight for use. At first, the medium was replaced with fresh DMEM medium, to which 100 mM trehalose (a compound capable of increasing the level of cell autophagy, as positive control), or 100 µg/mL the rare-earth upconversion nanophosphors (UCN, UCP, and UCN-S) was added, and an equal volume of PBS was added as negative control. After cell incubation of 24 hr, the fluorescence generated by GFP reporter gene was observed, imaged, and measured under a fluorescence microscope.

Figure 13:
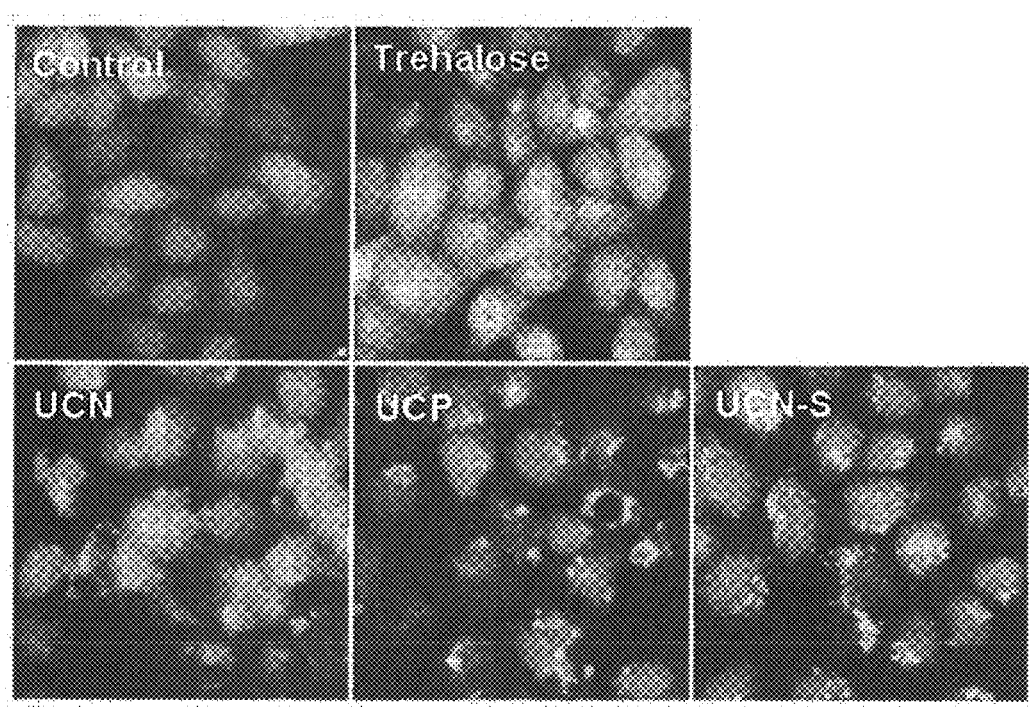
FIG. 13 is a photograph showing the autophagy induced by the rare-earth upconversion nanophosphors and the formation of GFP-LC3 dot-like aggregation.

The results showed that, all the rare-earth upconversion nanophosphors (UCN, UCP, and UCN-S) induced the autophagy and vacuolation of HeLa-LC3 cells to different extents. The ability of the three rare-earth upconversion nanophosphors to induce autophagy at the same dosage is as follows: UCP>UCN>UCN-S (FIG. 13).

Example 17

RE-1 Blocked the Ability of the Rare-Earth Upconversion Nanophosphors (UCN, UCP, UCN-S) to Induce Autophagy The rare-earth upconversion nanophosphors (UCN, UCP, UCN-S) coated with RE-1 were prepared as follows: 50 µg, 10 µg, and 350 µg RE-1 was mixed with 100 µg UCN, UCP, or UCN-S, respectively, incubated at 37° C. for 2 hr, centrifuged at 12000 rpm, and then washed with water for 3 times to remove the excess and unbound RE-1 peptides. The resultant precipitate was resuspended in 100 µL water.

HeLa-LC3 cells were inoculated into a 96-well cell culturing plate at a density of about $1$-$2\times10^4$ cells/well, and cultured overnight for further use. At first, the medium was replaced with fresh DMEM medium, to which UCN, UCP, or UCN-S with or without the coating of RE-1 peptides was added at different concentrations (0 µg/mL, 10 µg/mL, 100 µg/mL, 1000 µg/mL). After culturing for 24 hr, the fluorescence generated by GFP reporter gene was observed, imaged, and measured under a fluorescence microscope.

The ability to induce cell autophagy was estimated by determining the numbers of LC3 aggregates and vacuoles.

Figure 14A:
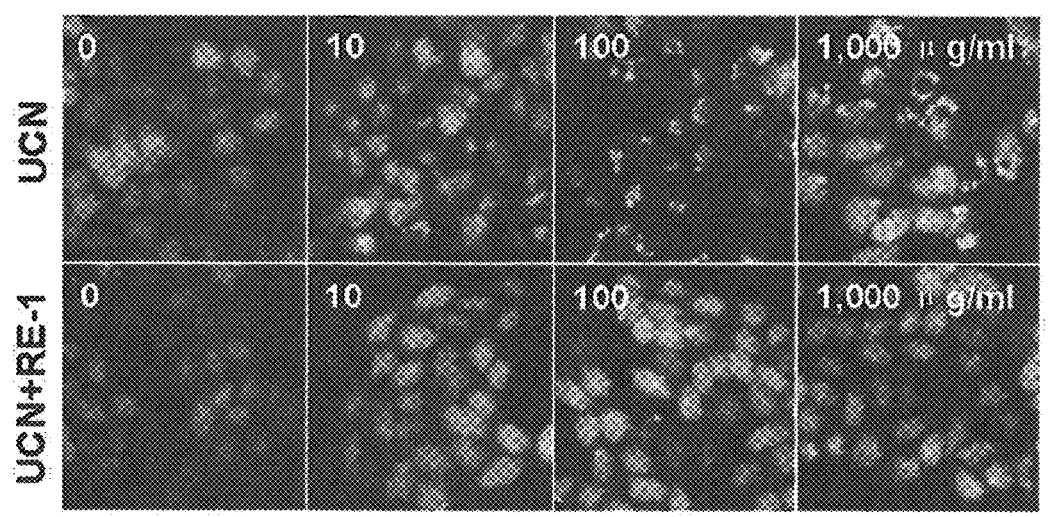
FIG. 14A, FIG. 14B, FIG. 14C, FIG. 14D, FIG. 14E, FIG. 14F, FIG. 14G, and FIG. 14H show that RE-1 reduced the autophagy induced by the rare-earth upconversion nanophosphors in a concentration-dependent way.
Figure 14B:
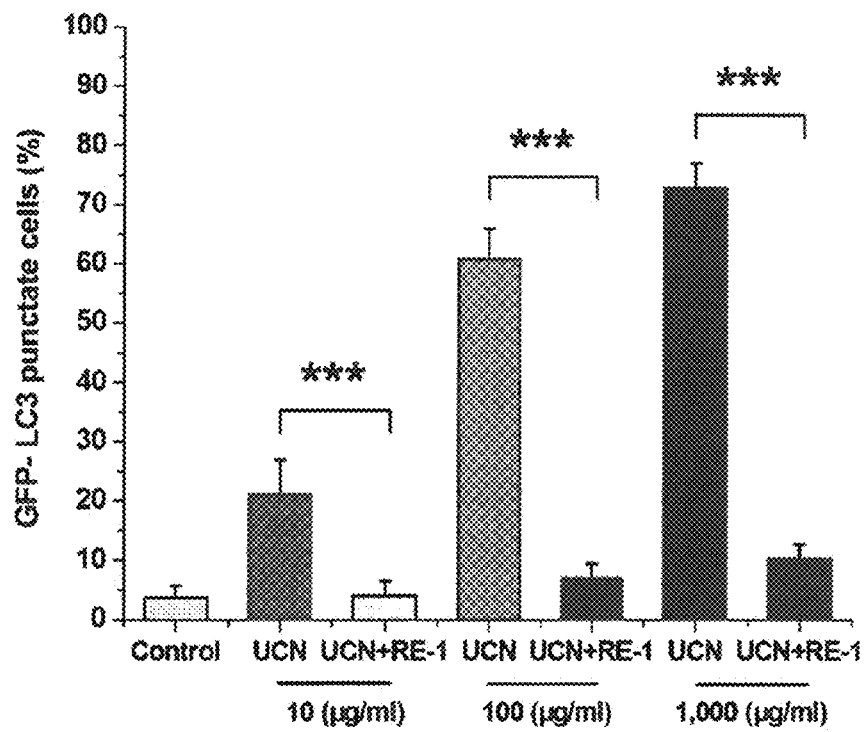
Figure 14C:
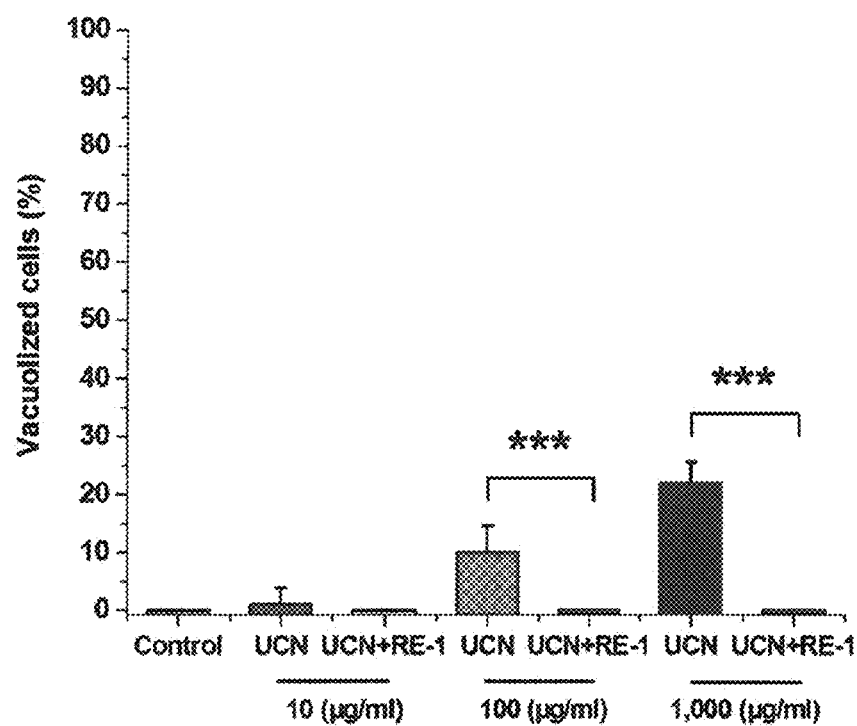
Figure 14D:
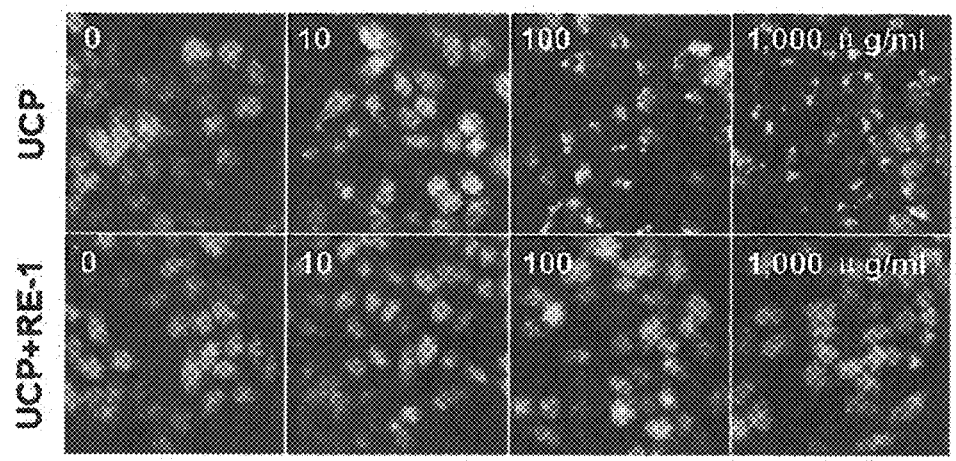
Figure 14E:
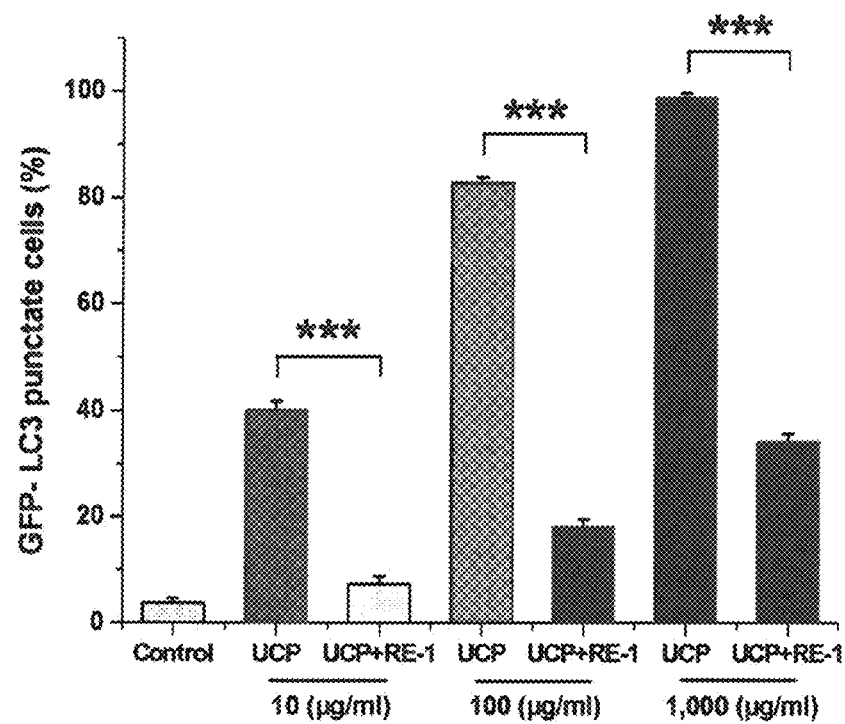
Figure 14F:
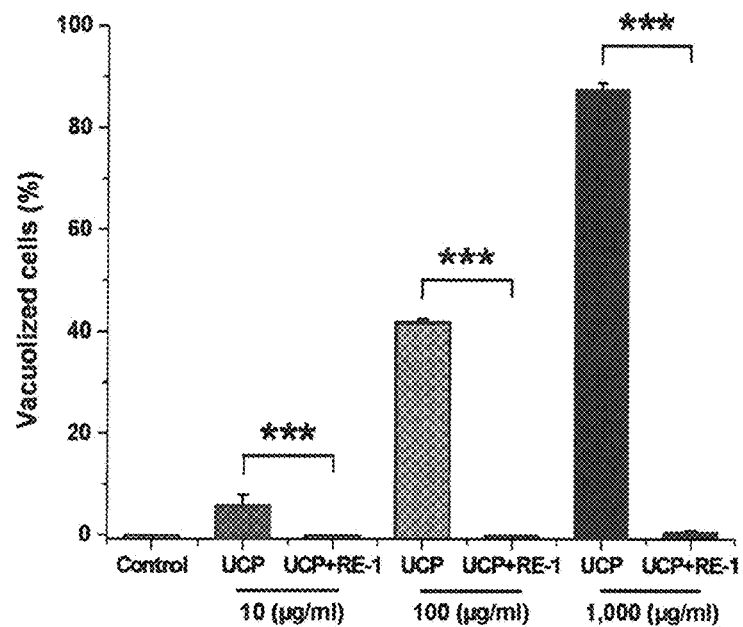
Figure 14G:
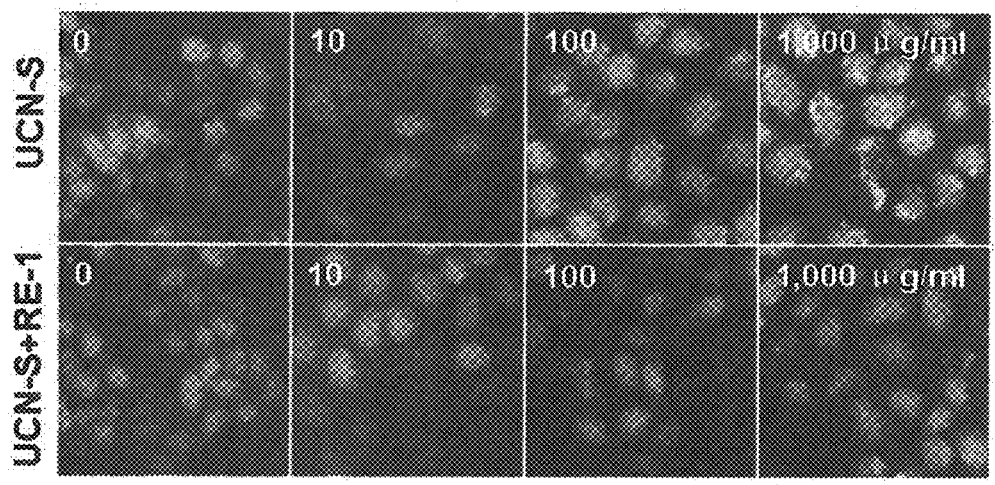
Figure 14H:
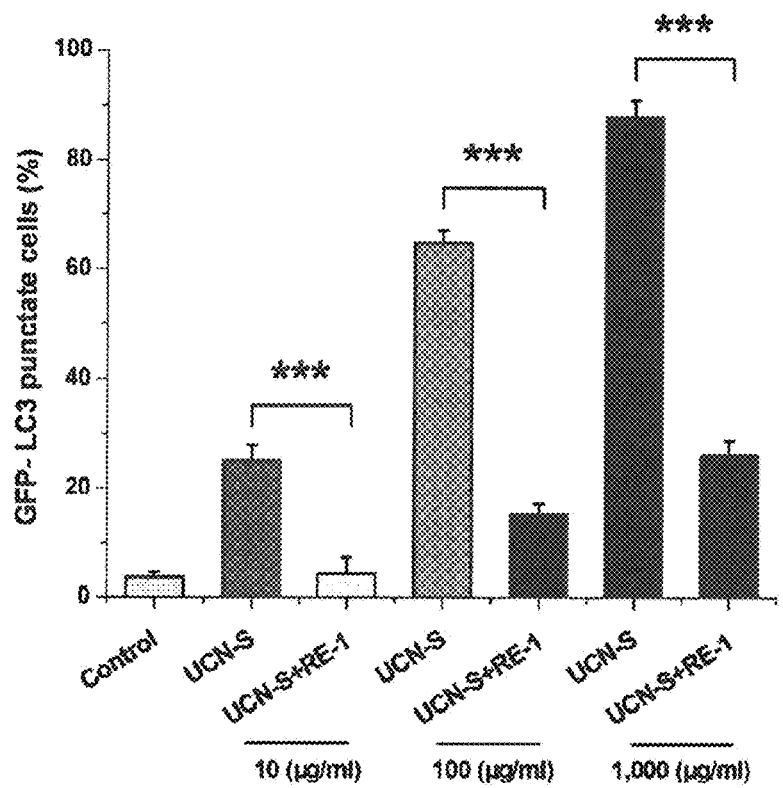

The results showed that, the ability of UCN, UCP, or UCN-S to induce cell autophagy increased as their dosages increased. UCN-S did not result in vacuolation. RE-1 significantly inhibited cell autophagy induced by UCN (FIG. 14A, FIG. 14B and FIG. 14C), UCP (FIG. 14D, FIG. 14E and FIG. 14F), and UCN-S (FIG. 14G and FIG. 14H). The experimental results were statistically significant.

Example 18

RE-1 Analogues Blocked the Ability of the Rare-Earth Upconversion Nanophosphors (UCN, UCP) to Induce Cell Autophagy UCN and UCP coated with RE-1 analogues RE-2, RE-3, or RE-5 were prepared as follows: 50 μg or 10 μg RE-1 analogues RE-2, RE-3, or RE-5 was mixed with 100 μg UCN or UCP, respectively, incubated at 37° C. for 2 hr, centrifuged at 12000 rpm, and then washed with water 3 times to remove the excess and unbound peptides. The resultant precipitate was resuspended in 100 μL water.

HeLa-LC3 cells were inoculated into a 96-well cell culture plate at a density of about $1-2\times10^4$ cells/well, and cultured overnight for further use. At first, the medium was replaced with fresh DMEM medium, and then 100 μg/mL UCN, UCN+RE-1, UCN+RE-2, UCN+RE-3, or UCN+RE-5 was added. An equal volume of PBS was used as blank. A mixture of 100 μg/mL UCN and 10 mg/mL PEG was used as negative control. A mixture of 100 mM trehalose and 50 μg RE-1 was used as positive control. After culturing for 24 hr, a fluorescence microscope was used to observe, image, and count.

HeLa-LC3 cells were inoculated into a 96-well cell culture plate at a density of about $1-2\times10^4$ cells/well, and cultured overnight for further use. At first, the medium was replaced with fresh DMEM medium, and then 100 μg/mL UCP, UCP+RE-1, UCP+RE-2, UCP+RE-3, or UCP+RE-5 was added. An equal volume of PBS was used as blank. After culturing for 24 hr, a fluorescence microscope was used to observe, image, and count.

The ability to induce cell autophagy was estimated by determining the numbers of LC3 aggregates and vacuoles.

Figure 15A:
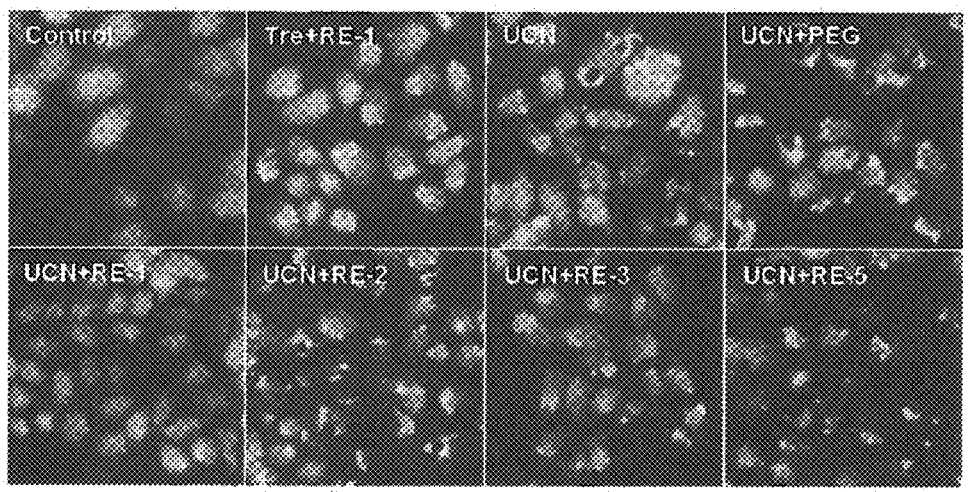
FIG. 15A, FIG. 15B, FIG. 15C, FIG. 15D, FIG. 15E, and FIG. 15F show the effect of RE-1 analogues on the autophagy induced by the rare-earth upconversion nanophosphors.
Figure 15B:
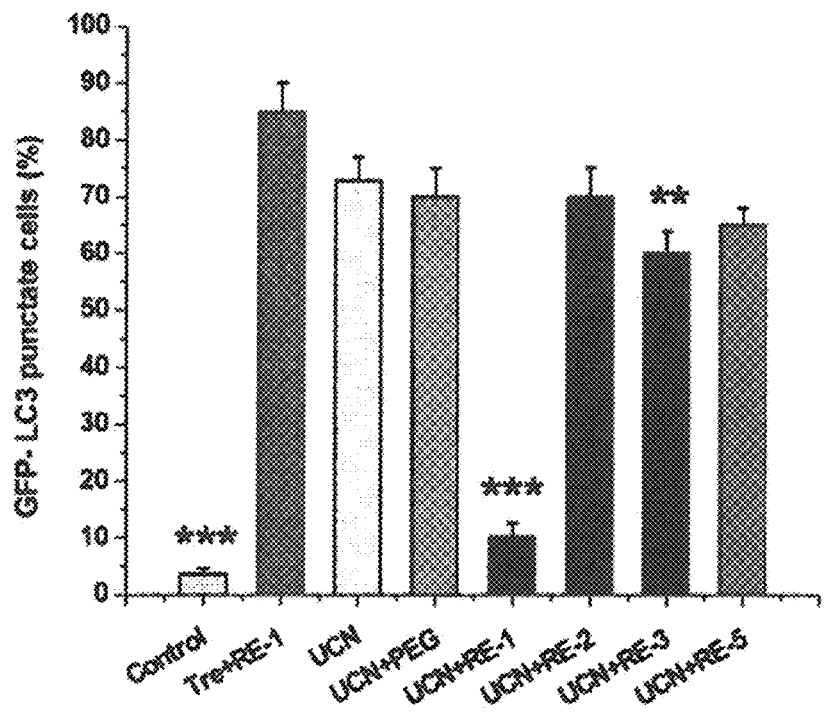
Figure 15C:
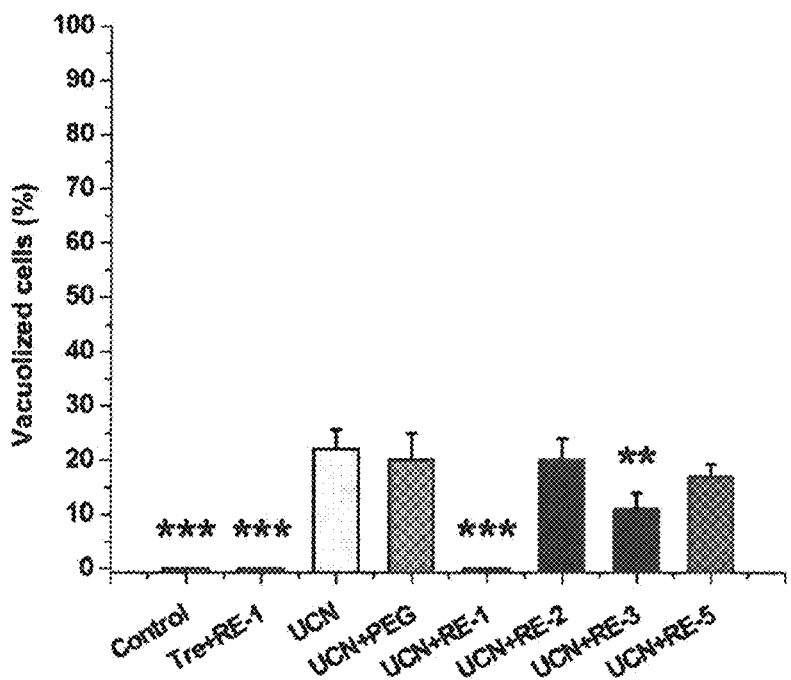
Figure 15D:
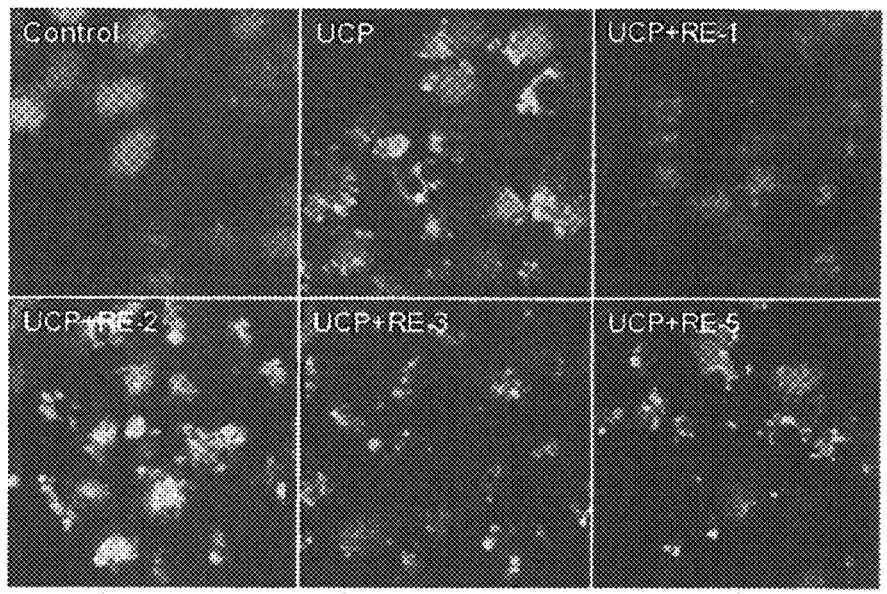
Figure 15E:
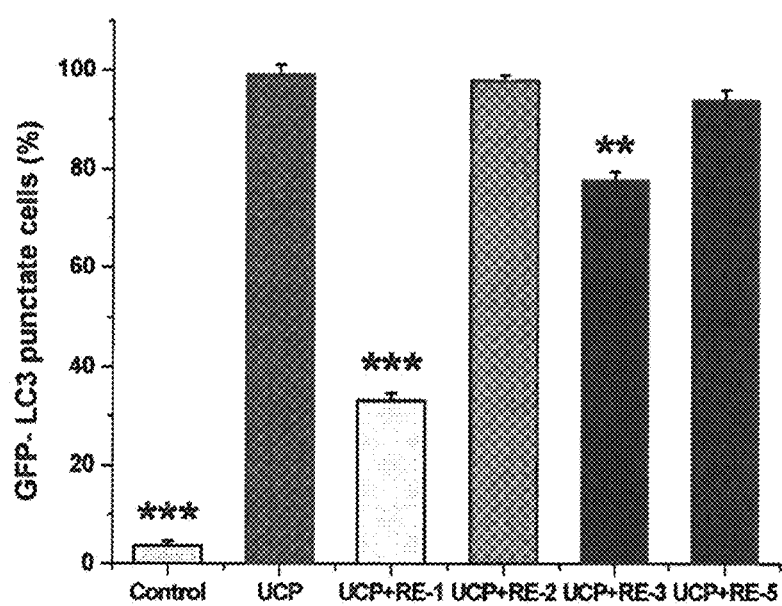
Figure 15F:
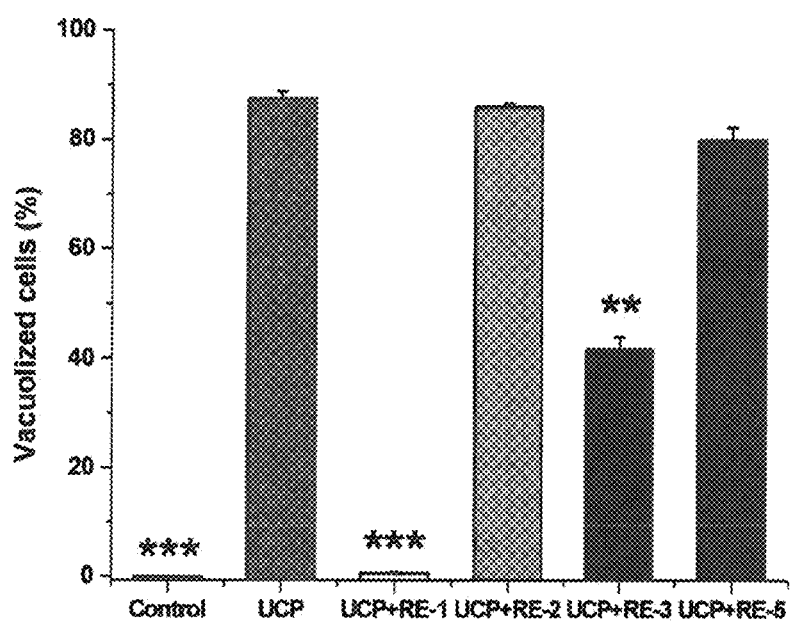

The results showed that, RE-2 and RE-5 did not inhibit GFP-LC3 dot-like aggregation and cytoplasm vacuolation in GFP-LC3/HeLa cells induced by UCN. The nonspecifically bounded PEG, used in the same way as RE-1, only had a slight inhibitory effect (no statistical significance) even at a concentration up to 100 mg/mL. For the control group treated with the mixture of Tre and RE-1, RE-1 short peptide had no inhibition on the cell autophagy induced by Tre, indicating that RE-1 short peptide per se did not affect the course of autophagy. However, the peptide analogue RE-3 exhibited an inhibitory effect on GFP-LC3 dot-like aggregation and cytoplasm vacuolation in GFP-LC3/HeLa cells induced by UCN. The statistical result showed that RE-3 reduced GFP-LC3 dot-like aggregation (by 21%) and cytoplasm vacuolation (by 50%) in GFP-LC3/HeLa cells induced by UCN. The results showed that the abilities of RE-1 analogues RE-2, RE-3, and RE-5 after coating UCN to inhibit the cell autophagy induced by UCN were different: RE-1>RE-3>RE-5, while RE-2 exhibited substantially no inhibitory effect. The results were statistically significant (FIG. 15A, FIG. 15B and FIG. 15C). Similar results for inhibiting cell autophagy were obtained for UCP coated with RE-1 analogues RE-2, RE-3, and RE-5 (FIG. 15D, FIG. 15E and FIG. 15F). These results further demonstrated that RE-1 short peptides could inhibit GFP-LC3 dot-like aggregation and cytoplasm vacuolation in GFP-LC3/HeLa cells induced by the rare-earth rare-earth upconversion nanophosphors without affecting the course of autophagy of the cells, and that such inhibition showed polypeptide specificity for RE-1 but not for its analogues RE-2 and RE-5, or for PEG.

Example 19

RE-1 Blocked the Ability of the Rare-Earth Upconversion Nanophosphors (UCN, UCP) to Induce Cell Autophagy HeLa cells were inoculated into a 24-well cell culturing plate at a density of about $3-5\times10^4$ cells/well, and cultured overnight for further use. At first, the medium was replaced with fresh DMEM medium, and then 100 μg/mL UCN or UCN+RE-1 was added. An equal volume of PBS was used as blank. A mixture of 100 μg/mL UCN and 10 mg/mL PEG was used as negative control. 100 mM trehalose was used as positive control. Then, western blotting assay was performed.

HeLa cells were inoculated into a 24-well cell culturing plate at a density of about $3-5\times10^4$ cells/well, and cultured overnight for further use. At first, the medium was replaced with fresh DMEM medium, and then 100 μg/mL UCP or UCP+RE-1 was added. An equal volume of PBS was used as blank. A mixture of 100 μg/mL UCP+AP-1 and a mixture of 400 μg/mL $TiO_2$+AP-1 were used as negative control. 400 μg/mL $TiO_2$ was used as positive control. Then, western blotting assay was performed.

Figure 16A:
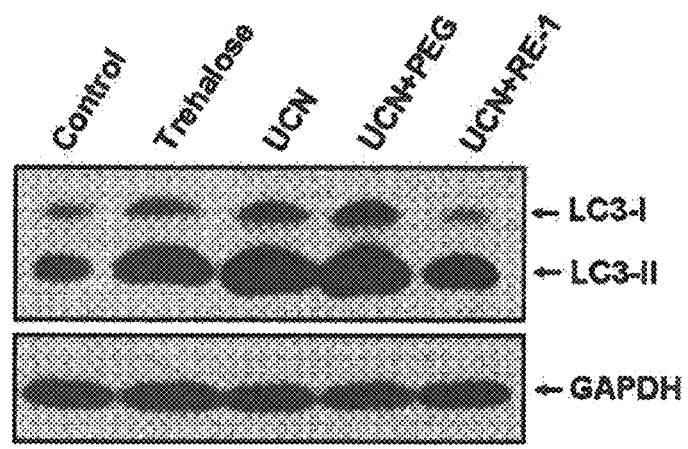
FIG. 16A and FIG. 16B are Western Blotting results showing that RE-1 reduced the autophagy induced by the rare-earth upconversion nanophosphors.
Figure 16B:
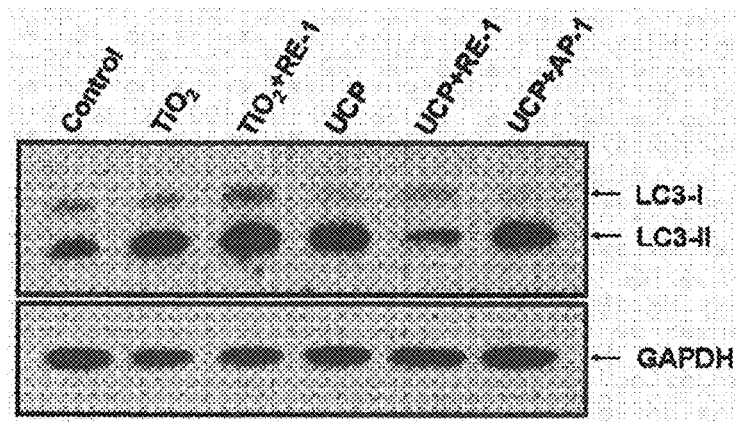

The results showed that, when autophagy occurred, the marker protein for autophagy, LC3 was subjected to type I cleavage (18 KD) and type II cleavage (16 KD); both UCN and UCP increased the level of cell autophagy (significantly increased LC3 II), while UCN and UCP coated with RE-1 significantly prevented the increase of LC3 II. The results indicated that, RE-1 effectively inhibited the ability of UCN and UCP to induce cell autophagy, and that such inhibition showed specificity for RE-1 but not for AP-1. Similarly, RE-1 only inhibited the ability of UCN and UCP to induce cell autophagy, but could not inhibit the cell autophagy induced by $TiO_2$ (FIG. 16A: UCN; FIG. 16B: UCP).

Example 20

RE-1 Blocked the Formation of Autophagosome Induced by the Rare-Earth Upconversion Nanophosphors (UCN, UCP)

HeLa cells were inoculated into a 24-well cell culturing plate at a density of about $3-5\times10^4$ cells/well, and cultured overnight for further use. At first, the medium was replaced with fresh DMEM medium, and then 100 μg/mL UCN, UCP, UCN+RE-1, or UCP+RE-1 was added. An equal volume of PBS was used as blank. After culturing for 24 hr, the cells were collected and in situ fixed with 2.5% glutaral-dimethyl arsine buffer (pH 7.4) at 4° C. for 1 hr, then fixed with 2% osmium tetroxide at room temperature for 1 hr, and then dehydrated with ethanol gradients. Then, the cell samples were embedded into epoxy resin (EPON812). The embedded cell samples were cut into ultrathin slices, which were stained with uranyl acetate and lead citrate, and observed and imaged under a transmission electron microscope (JEOL-1230, JEOL, Japan).

Figure 17A:
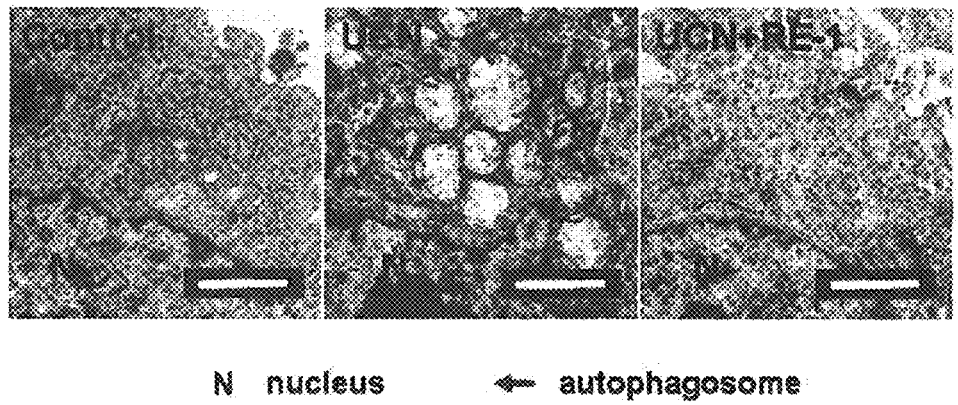
FIG. 17A and FIG. 17B are transmission electron micrographs showing that RE-1 reduced the formation of autophagosome induced by the rare-earth upconversion nanophosphors in cells.
Figure 17B:
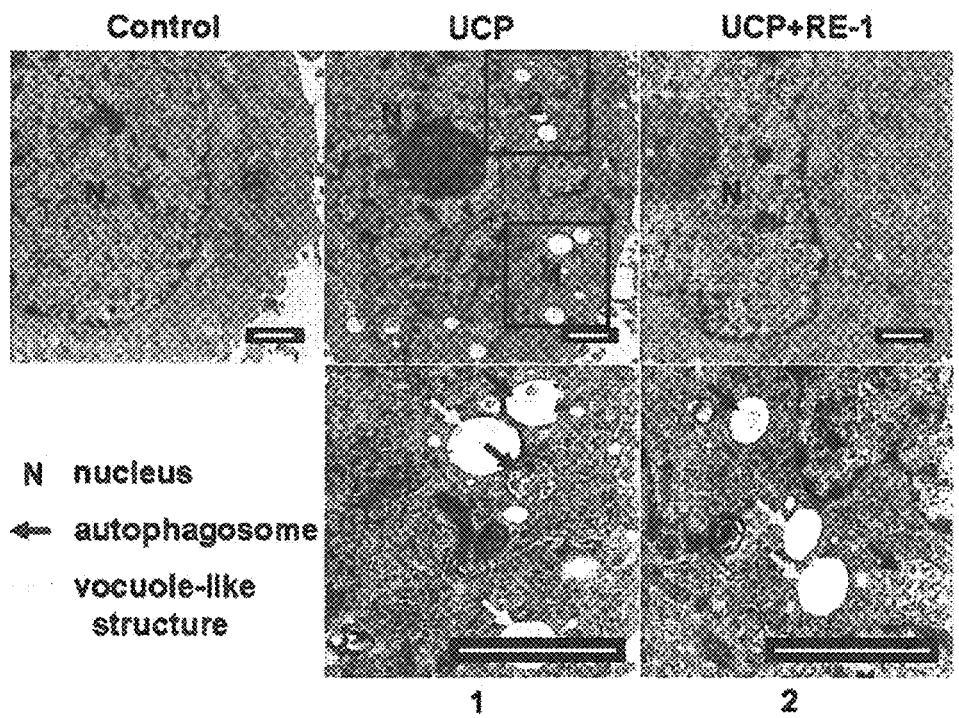

The results showed that, for UCN- and UCP-treated groups, a large number of autophagosomes and vacuoles were formed in the cells, while for UCN+RE-1- and UCP+RE-1-treated group, no such phenomenon was observed. The results indicated that RE-1 significantly inhibited autophagosome formation induced by the rare-earth upconversion nanophosphors (UCN, UCP) (FIG. 17A: UCN; FIG. 17B: UCP).

Example 21

RE-1 Blocked the Cell Autophagy Induced by the Rare-Earth Upconversion Nanophosphors (UCN, UCP) in Mice Livers Balb/c mice (purchased from SLAC Laboratory Animal (Shanghai, China), 6 weeks old, and weighed 20 g when used) were bred in a sterile housing, and then 300 μg (dosage: 15 mg/kg) UCN, UCN+PEG (containing 10 mg PEG), UCN+RE-1, UCP, UCP+RE-1, or UCP+AP-1 was injected through tail vein. An equal volume of normal saline was injected as a control. After 24 hr, the livers of the mice were removed and subjected to western blotting assay.

Figure 18A:
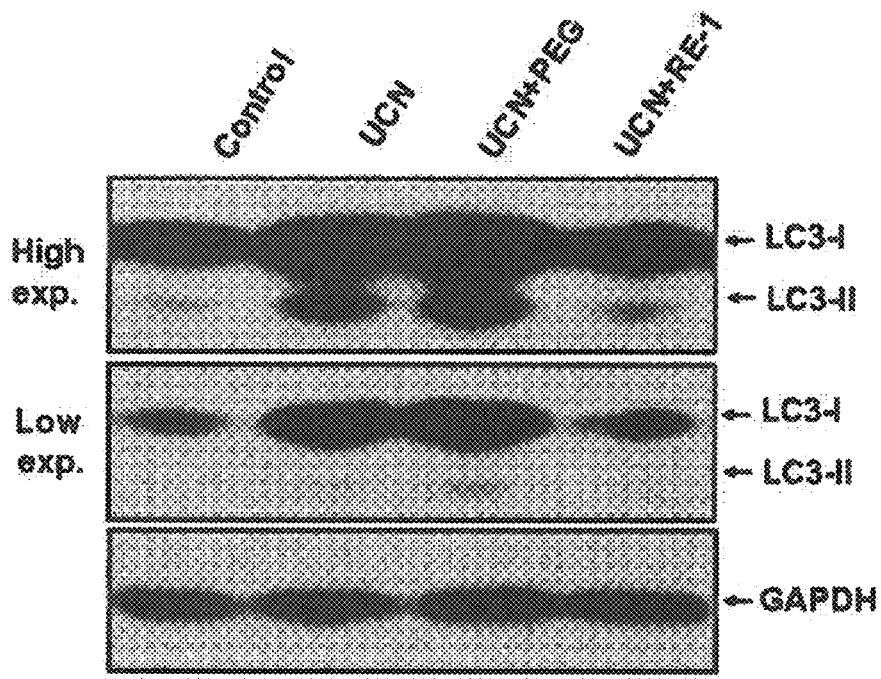
FIG. 18A and FIG. 18B are Western Blotting results showing that RE-1 reduced the autophagy in mice liver induced by the rare-earth upconversion nanophosphors.
Figure 18B:
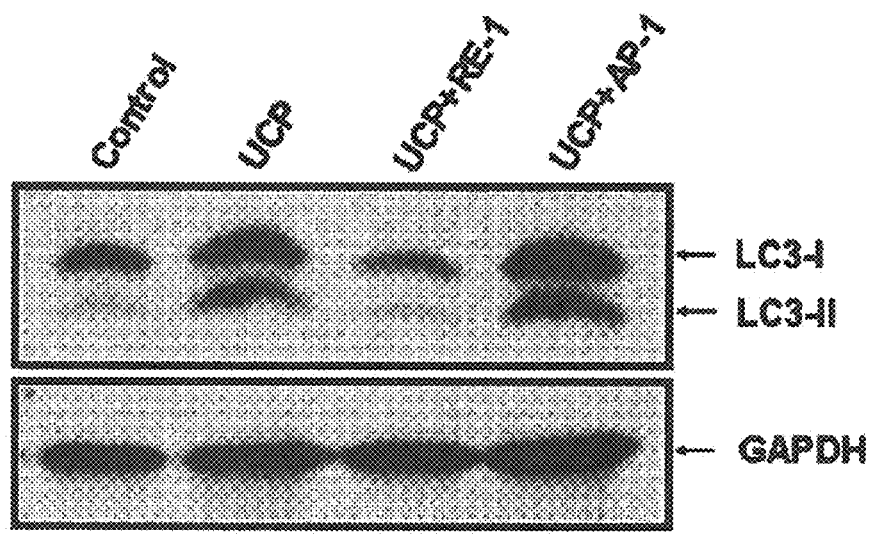

The results showed that, both UCN and UCP increased the level of autophagy in mice liver (significantly increased LC3 type II), while the coating of RE-1 significantly prevented the increase of LC3 type II. The results indicated that RE-1 effectively inhibited the ability of UCN and UCP to induce cell autophagy. However, PEG could not inhibit the ability of UCN to induce autophagy in liver. Similarly, AP-1 could not inhibit the ability of UCP to induce autophagy in liver (FIG. 18A: UCN; FIG. 18B: UCP).

Example 22

RE-1 Blocked the Formation of Autophagosome Induced by the Rare-Earth Upconversion Nanophosphors (UCN, UCP) in Mice Livers The mice livers obtained as described in Example 21 were in situ fixed with 2.5% glutaral-dimethyl arsine buffer (pH 7.4) at 4° C. for 1 hr, then fixed with 2% osmium tetroxide at room temperature for 1 hr, and then dehydrated with ethanol gradients. Then, the cell samples were embedded into epoxy resin (EPON812). The embedded cell samples were cut into ultrathin slices, which were stained with uranyl acetate and lead citrate, and observed and imaged under a transmission electron microscope (JEOL-1230, JEOL, Japan).

Figure 19A:
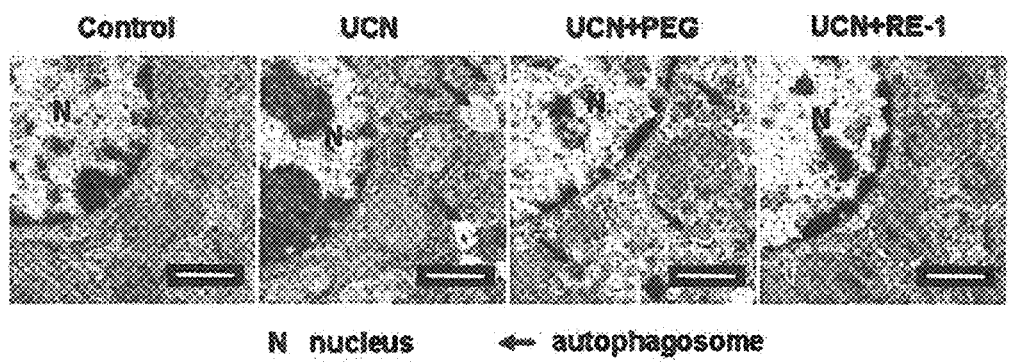
FIG. 19A and FIG. 19B are transmission electron micrographs showing that RE-1 reduced the formation of autophagosome induced by the rare-earth upconversion nanophosphors in mice liver.
Figure 19B:
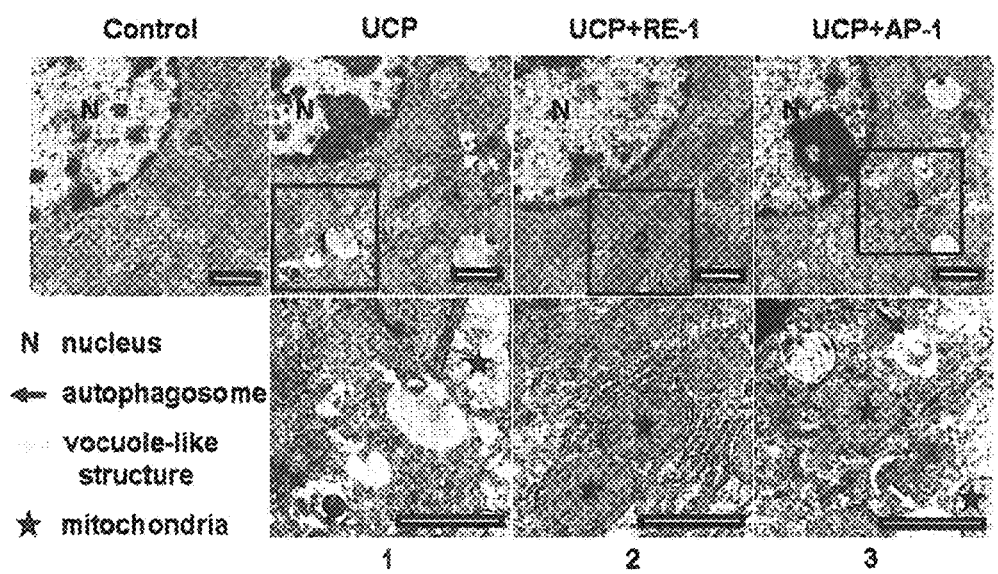

The results showed that, for UCN- and UCP-treated groups, a large number of autophagosomes and vacuoles were formed in the liver cells and the cytoplasm was dispersed, the mitochondrion was broken or its content was lost significantly, while for UCN+RE-1- and UCP+RE-1-treated groups, no such phenomenon was observed. The results indicated that RE-1 significantly inhibited autophagosome formation induced by the rare-earth upconversion nanophosphors (UCN, UCP) in liver, thereby inhibiting autophagy, while PEG and AP-1 did not (FIG. 19A: UCN; FIG. 19B: UCP).

Example 23

RE-1 Reduced the Cytotoxicity Induced by the Rare-Earth Upconversion Nanophosphors (UCN, UCP) in HeLa Cells HeLa cells were inoculated into a 96-well cell culturing plate at a density of about $1-2 \times 10^4$ cells/well, and cultured overnight for further use. At first, the medium was replaced with fresh DMEM medium, and then 10 μg/mL, 100 μg/mL, 250 μg/mL, 500 μg/mL, or 1000 μg/mL of UCN or UCP coated, with or without RE-1, were added, respectively. After culturing for 24 hr, MTT cell viability assay and PI staining were performed to detect the mortality of the cells.

Figure 20A:
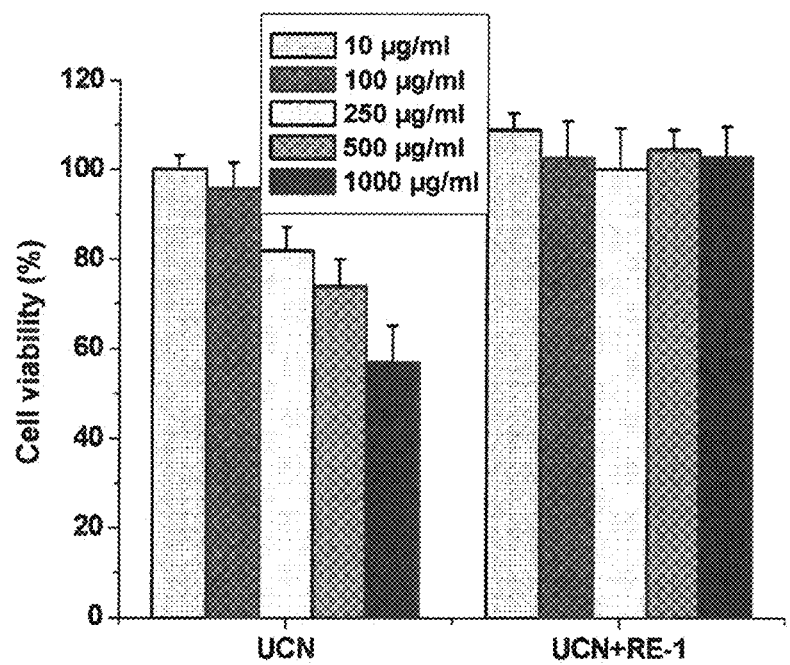
FIG. 20A, FIG. 20B, FIG. 20C, and FIG. 20D show that RE-1 reduced toxicity induced by the rare-earth upconversion nanophosphors in HeLa cells.
Figure 20B:
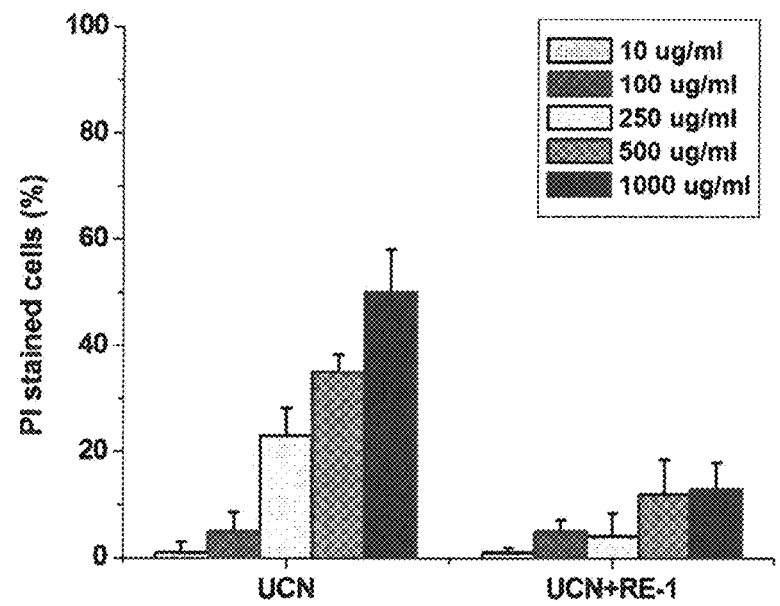
Figure 20C:
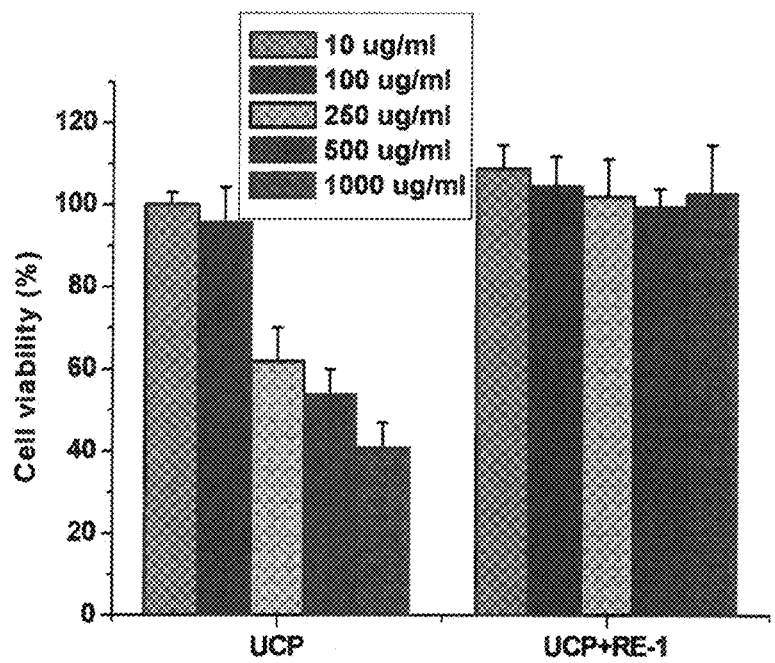
Figure 20D:
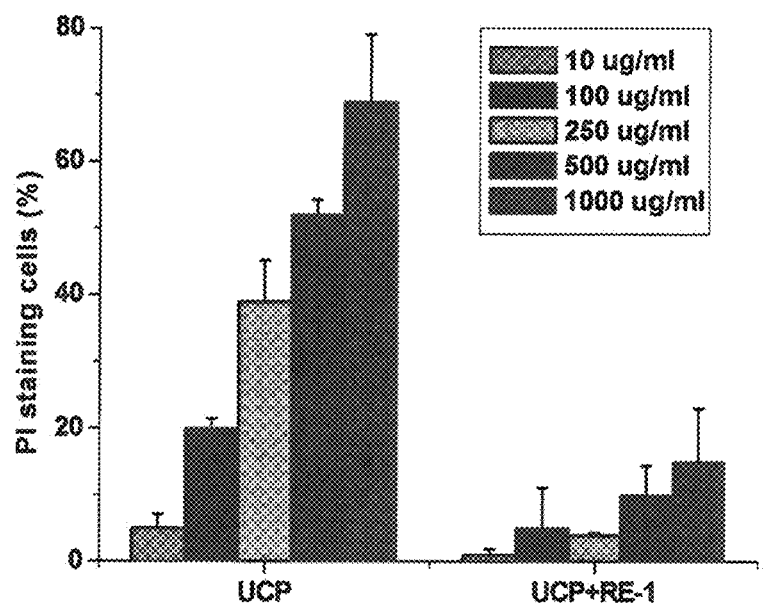

The results showed that, both UCN- and UCP-treatments resulted in higher cell mortality, and the cytotoxicity induced by the nanomaterials increased as the concentration of the nanomaterials increased. Coating with RE-1 significantly reduced cytotoxicity. The results indicated that RE-1 effectively improved the biological safety of the rare-earth upconversion nanophosphors (FIG. 20A: MTT result for UCN; FIG. 20B: PI staining result for UCN; FIG. 20C: MTT result for UCP; FIG. 20D: PI staining result for UCP).

Example 24

Detection of the Effect of RE-1 Analogues on the Cytotoxicity Induced by the Rare-Earth Upconversion Nanophosphors (UCN, UCP) in HeLa Cells HeLa cells were inoculated into 96-well cell culturing plate at a density of about $1-2 \times 10^4$ cells/well, and cultured overnight for further use. At first, the medium was replaced with fresh DMEM medium, and then 1 mg/mL UCN, UCP, UCN+PEG (containing 10 mg PEG), UCN+RE-1, UCP, UCP+RE-1, UCN+RE-2, UCN+RE-3, UCN+RE-5, UCP+RE-2, UCP+RE-3, or UCP+RE-5 were added, respectively. After culturing for 24 hr, MTT cell viability assay and PI staining were performed to detect the mortality of the cells.

Figure 21A:
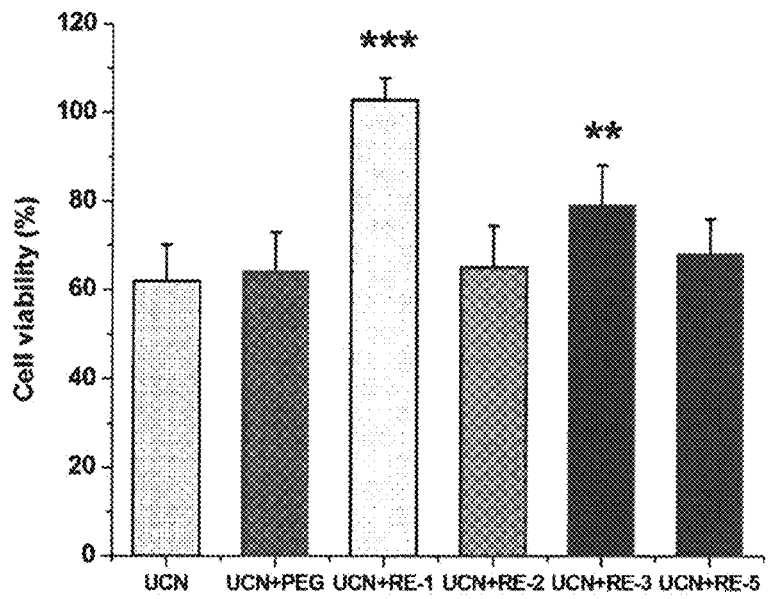
FIG. 21A and FIG. 21B show the effect of RE-1 analogues on the toxicity induced by the rare-earth upconversion nanophosphors in HeLa cells.
Figure 21B:
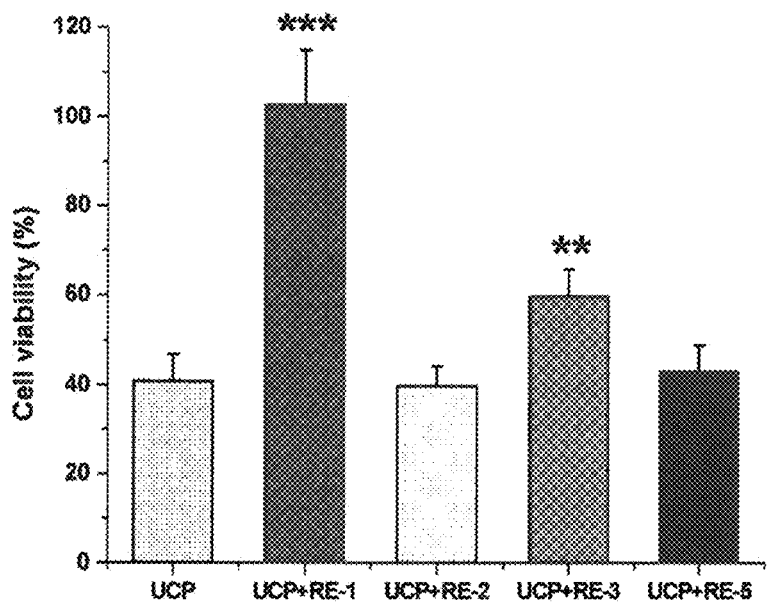

The results showed that, the coating of RE-1 analogues RE-2, RE-3, RE-5 exhibited different inhibitory effects on cytotoxicity induced by UCN and UCP: RE-1>RE-3>RE-5, while RE-2 nearly showed no inhibitory effect. The results had statistical significance (FIG. 21A: UCN; FIG. 21B: UCP). The results indicated that inhibition of RE-1 on the cytotoxicity induced by the rare-earth upconversion nanophosphors showed specificity for sequences. As compared with RE-1, the analogue RE-2 had a different sequence, with two cysteine deletions, and thus showed no inhibitory effect. This result further demonstrated that the two cysteines at both sides of RE-1 were very important for the binding of RE-1 short peptide to $Nd_2O_3$ nanoparticles.

Example 25

RE-1 Blocked the Liver Damage Induced by UCP in Mice Livers

The mice livers obtained as described in Example 21 were in situ fixed with 2.5% glutaral-dimethyl arsine buffer (pH 7.4) at 4° C. for 1 hr, then fixed with 2% osmium tetroxide at room temperature for 1 hr, and then dehydrated with ethanol gradients. Then, the cell samples were embedded in paraffin. The embedded cell samples were cut into ultrathin slices, which were stained with HE (hematoxylin-eosin), and observed and imaged under fluorescence microscope.

Figure 22:
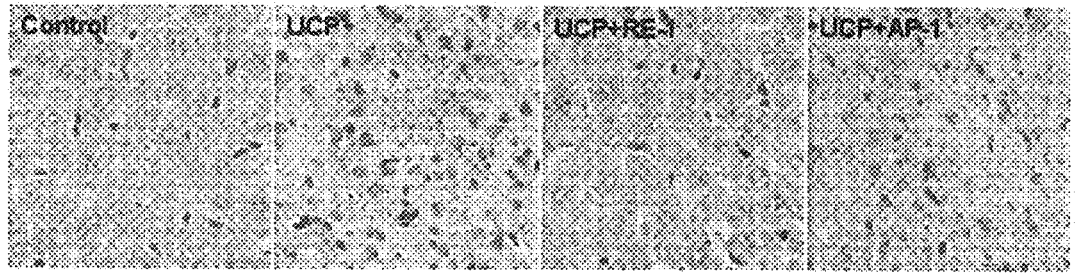
FIG. 22 shows that RE-1 reduced liver damage induced by UCP in mice liver.

The results showed that, for UCP- and UCP+AP-1-treated groups, the livers were dispersed, there appeared severe inflammatory cell infiltration, and most of the liver cells were in a state of apoptosis or death; while for UCP+RE-1-treated group, the liver cells were intact and in a good state. The results indicated that UCP could damage liver tissue, and coating with RE-1 significantly reduced the level of the damages to livers, while AP-1 showed no such effect (FIG. 22).

Example 26

RE-1-RGD Increased the Ability of the Rare-Earth Upconversion Nanophosphors UCN to Specifically Adhere to HeLa Cells HeLa cells were cultured on a coverslip (22 mm×22 mm), which was then placed into a 6-well plate with the cells facing upward or downward, and the coverslip was supported by a sterilized glass cube (2 mm×2 mm×2 mm). Then, 4 mL of DMEM medium containing the rare-earth upconversion nanophosphors coated with RE-1 or RE-1-RGD or without any coating was slowly poured into the 6-well plate, such that the cells were fully immersed in the medium, and the coverslip was just located at the middle of the height of the liquid. The cells were placed into a cell incubator at 37° C. for 2 hr, and then washed with PBS 3 times. The UCNs adhered to the surfaces of the cells were observed under a fluorescence microscope (Olympus IX71, Olympus, Japan) equipped with a 980-nm infrared laser (MDL-980 nm 1 W, Changchun New Industries Optoelectronics Tech. Co., Ltd, China).

Figure 23:
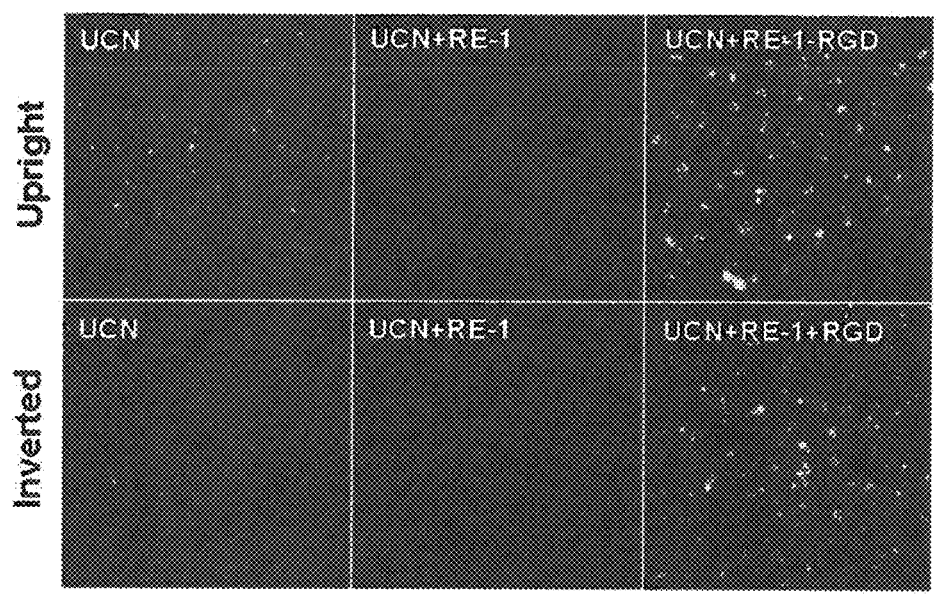
FIG. 23 shows that RE-1-RGD increased the specific adherence of rare-earth upconversion nanophosphors UCN to HeLa cells.

The results showed that, for the group treated with the rare-earth upconversion nanophosphors without RE-1 coating, there was a large number of nonspecifically adhered nanoparticles; for the group treated with the rare-earth upconversion nanophosphors coated with RE-1, the number of the upconversion nanophosphors adhered to the surface of the cells was greatly reduced; and for the group treated with the rare-earth upconversion nanophosphors coated with RE-1-RGD, the number of the upconversion nanophosphors adhered to the surface of the cells was significantly higher than the above two groups. The results indicated that, RE-1-RGD, which contained a tumor cell-targeting sequence RGD, significantly increased the adherence ability of UCN to HeLa cells (FIG. 23).

Example 27

RE-1-RGD Increased the Ability of the Rare-Earth Upconversion Nanophosphors UCN to Induce Autophagy UCN coated with RE-1-RGD was prepared as follows: 50 μg RE-1-RGD and 100 μg UCN were mixed, incubated at 37° C. for 2 hr, and then centrifuged at 12000 rpm. The resultant precipitate was washed with water for 3 times to remove the excess and unbound RE-1-RGD peptides. Then, the precipitate was resuspended in 100 μL water for further use.

HeLa-LC3 cells were inoculated into a 96-well cell culture plate at a density of about $1-2 \times 10^4$ cells/well, and cultured overnight for further use. At first, the medium was replaced with fresh DMEM medium, and then 100 μg/mL UCN, UCN+RE-1, and UCN+RE-1-RGD were added, respectively. An equal volume of PBS was used as blank. After culturing for 24 hr, LC3 dot-like aggregates and vacuoles in the cells were observed and imaged under a fluorescence microscope.

Figure 24A:
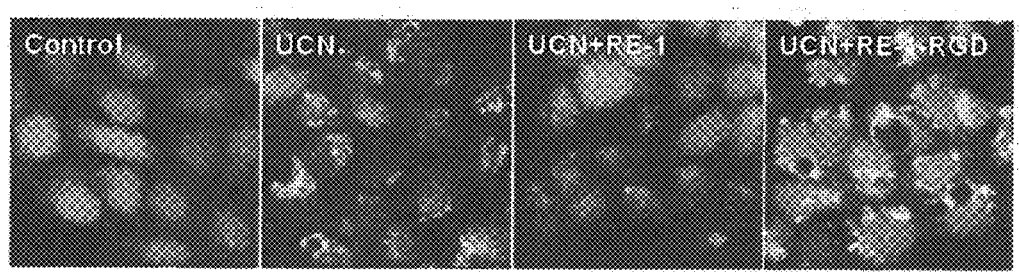
FIG. 24A and FIG. 24B show that RE-1-RGD increased the autophagy induced by the rare-earth upconversion nanophosphors UCN.

The results showed that, LC3 dot-like aggregates and vacuoles in the cells in the group treated with RE-1-RGD-coated UCN were significantly increased compared to the group treated with UCN, indicating that RE-1-RGD could specifically target to the cells, and thus increased autophagy and the therapeutic effect of UCN (FIG. 24A).

HeLa cells were inoculated into 24-well cell culture plate at a density of about $3-5 \times 10^4$ cells/well, and cultured overnight for further use. At first, the medium was replaced with fresh DMEM medium, and then 100 μg/mL UCN, UCN+PEG (containing 10 mg PEG), UCN+RE-1, and UCN+RE-1-RGD were added, respectively. An equal volume of PBS was used as blank. 100 mM trehalose was used as positive control. Then, western blotting assay was performed.

Figure 24B:
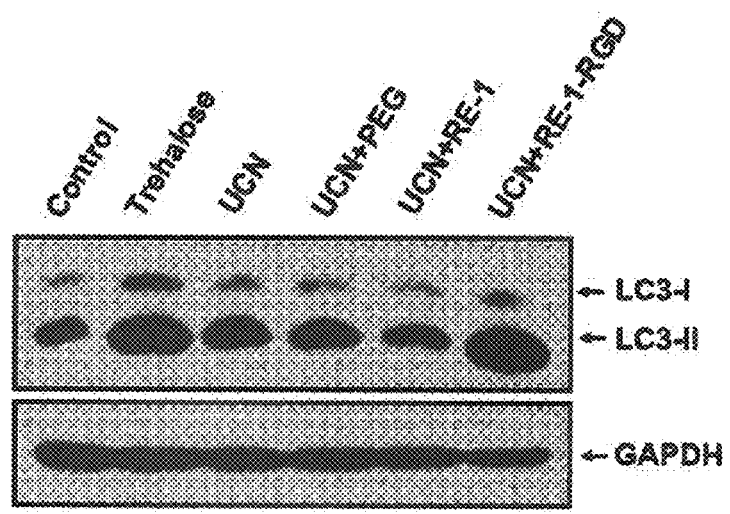

The results showed that, for the group treated with RE-1-RGD-coated UCN, LC3 II significantly increased in the cells, indicating that RE-1-RGD could significantly increase the ability of UCN to induce autophagy (FIG. 24B).

Example 28

RE-1-RGD could Increase the Cytotoxicity Induced by UCN in HeLa Cells

HeLa cells were inoculated into 96-well cell culturing plate at a density of about $1-2 \times 10^4$ cells/well, and cultured overnight for further use. At first, the medium was replaced with fresh DMEM medium, and then 1 mg/mL UCN, UCN+RE-1, and UCN+RE-1-RGD were added, respectively. After culturing for 24 hr, MTT cell viability assay and PI staining were performed to detect the mortality of the cells.

Figure 25A:
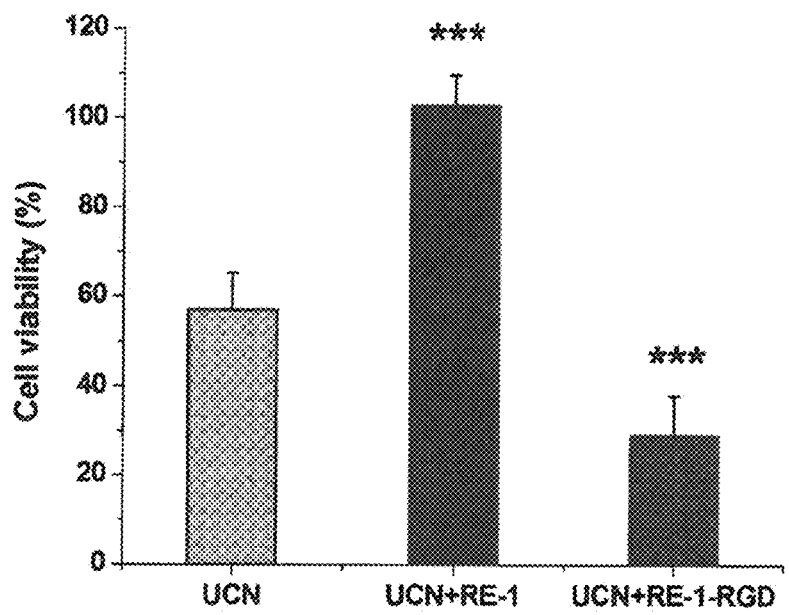
FIG. 25A and FIG. 25B show that RE-1-RGD increased cytotoxicity induced by UCN in HeLa cells.
Figure 25B:
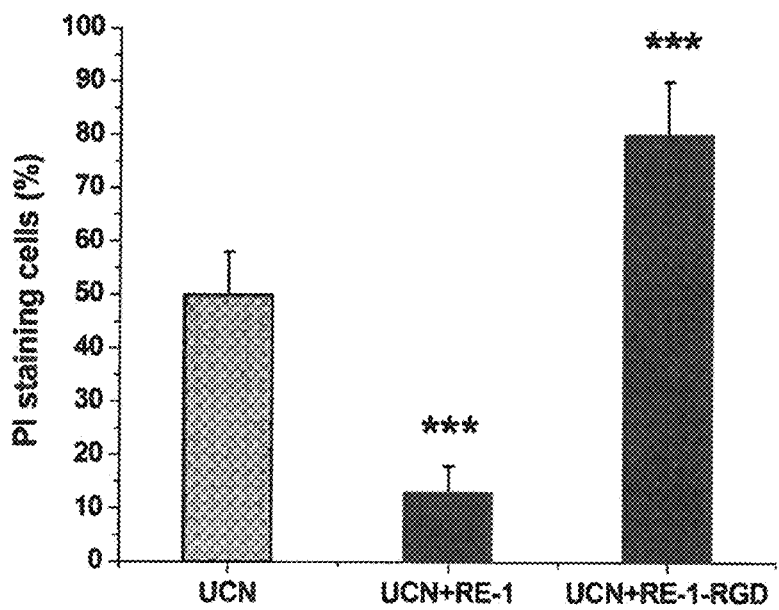

The results showed that, for the group treated with RE-1-RGD-coated UCN, the cell mortality was significantly higher compared to the group treated with UCN, indicating that RE-1-RGD could increase the cytotoxicity induced by UCN in HeLa cells, and thus effectively increased the ability of UCN to kill tumor cells (FIG. 25A: MTT results; FIG. 25B: PI staining results).

---

The invention claimed is:
1. A polypeptide specifically binding to a rare-earth nanoparticle, wherein the polypeptide comprises an amino acid sequence selected from the group consisting of SEQ ID NO: 2, SEQ ID NO: 3, SEQ ID NO: 4, SEQ ID NO: 5, SEQ ID NO: 7, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, and SEQ ID NO: 31.

2. The polypeptide of claim 1 comprising the amino acid sequence of SEQ ID NO: 2.

3. The polypeptide of claim 1 comprising the amino acid sequence of SEQ ID NO: 3.

4. The polypeptide of claim 1 comprising the amino acid sequence of SEQ ID NO: 4.

5. The polypeptide of claim 1 comprising the amino acid sequence of SEQ ID NO: 5.

6. The polypeptide of claim 1 comprising the amino acid sequence of SEQ ID NO: 7.

7. The polypeptide of claim 1 comprising the amino acid sequence of SEQ ID NO: 9.

8. The polypeptide of claim 1 comprising the amino acid sequence of SEQ ID NO: 10.

9. The polypeptide of claim 1 comprising the amino acid sequence of SEQ ID NO: 11.

10. The polypeptide of claim 1 comprising the amino acid sequence of SEQ ID NO: 12.

11. The polypeptide of claim 1 comprising the amino acid sequence of SEQ ID NO: 13.

12. The polypeptide of claim 1 comprising the amino acid sequence of SEQ ID NO: 14.

13. The polypeptide of claim 1 comprising the amino acid sequence of SEQ ID NO: 15.

14. The polypeptide of claim 1 comprising the amino acid sequence of SEQ ID NO: 17.

15. The polypeptide of claim 1 comprising the amino acid sequence of SEQ ID NO: 19.

16. The polypeptide of claim 1 comprising the amino acid sequence of SEQ ID NO: 21.

17. The polypeptide of claim 1 comprising the amino acid sequence of SEQ ID NO: 23.

18. The polypeptide of claim 1 comprising the amino acid sequence of SEQ ID NO: 25.

19. The polypeptide of claim 1 comprising the amino acid sequence of SEQ ID NO: 27.

20. The polypeptide of claim 1 comprising the amino acid sequence of SEQ ID NO: 29.

21. The polypeptide of claim 1 comprising the amino acid sequence of SEQ ID NO: 31.

22. A method for regulating the in vivo or in vitro autophagy and toxicity of rare-earth nanoparticles, comprising mixing and incubating the polypeptide of claim 1 with rare-earth nanoparticles, wherein the polypeptide specifically binds to the nanoparticles, and wherein the rare-earth nanoparticles comprise a rare earth element.

23. The method of claim 22, wherein the regulating reduces the toxicity of rare-earth nanoparticles.

* * * * *